US011020461B2

(12) United States Patent
Wasilewski et al.

(10) Patent No.: US 11,020,461 B2
(45) Date of Patent: Jun. 1, 2021

(54) METHODS AND COMPOSITIONS FOR CNS DELIVERY OF ARYLSULFATASE A

(71) Applicant: Shire Human Genetic Therapies, Inc., Lexington, MA (US)

(72) Inventors: Margaret Wasilewski, Lexington, MA (US); Anna Wijatyk, Lexington, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 15/999,472

(22) PCT Filed: Feb. 17, 2017

(86) PCT No.: PCT/US2017/018440
§ 371 (c)(1),
(2) Date: Aug. 17, 2018

(87) PCT Pub. No.: WO2017/143233
PCT Pub. Date: Aug. 24, 2017

(65) Prior Publication Data
US 2020/0179492 A1    Jun. 11, 2020

Related U.S. Application Data

(60) Provisional application No. 62/453,864, filed on Feb. 2, 2017, provisional application No. 62/296,563, filed on Feb. 17, 2016.

(51) Int. Cl.
*A61K 38/46* (2006.01)
*A61P 25/28* (2006.01)
*A61K 9/00* (2006.01)

(52) U.S. Cl.
CPC .......... *A61K 38/465* (2013.01); *A61K 9/0019* (2013.01); *A61K 9/0085* (2013.01); *A61P 25/28* (2018.01)

(58) Field of Classification Search
None
See application file for complete search history.

(56) References Cited

U.S. PATENT DOCUMENTS

| 8,545,837 | B2 * | 10/2013 | Zhu | A61K 9/0085 |
| | | | | 424/94.3 |
| 9,283,181 | B2 * | 3/2016 | Calias | A61P 1/08 |
| 9,320,711 | B2 * | 4/2016 | Natoli | C12N 9/14 |
| 9,770,410 | B2 * | 9/2017 | Salamat-Miller | A61P 25/28 |
| 2012/0009171 | A1 * | 1/2012 | Salamat-Miller | A61K 47/02 |
| | | | | 424/94.3 |

FOREIGN PATENT DOCUMENTS

WO    2011/163650 A2    12/2011

OTHER PUBLICATIONS

Kruse et al., Alterations of brain metabolites in metachromatic leukodystrophy as detected by localized proton magnetic resonance spectroscopy, 1993, J Neurol 241:68-74 (Year: 1993).*
Black et al., Metachromatic Leukodystrophy: A Model for the Study of Psychosis, 2003, J Neuropsychiatry Clin Neurosci 15(3):289-293 (Year: 2003).*
Bobo, et al., "Convection-enhanced delivery of macromolecules in the brain", Proc. Natl. Acad. Sci. USA, vol. 91, pp. 2076-2080, (1994).
Nguyen, et al., "Convective distribution of macromolecules in the primate brain demonstrated using computerized tomography and magnetic resonance imaging", J. Neurosurg. vol. 98, pp. 584-590, (2003).
Dali et al., "Intrathecal delivery of recombinant human arylsulfatase A in children with late-infantile metachromatic leukodystrophy", Molecular Genetics and Metabolism , vol. 117 , Issue 2 , S38 (2016).

* cited by examiner

*Primary Examiner* — John D Ulm
(74) *Attorney, Agent, or Firm* — Proskauer Rose LLP; Fangli Chen

(57) ABSTRACT

Provided are methods of treating metachromatic leukodystrophy comprising administering to a subject in need of treatment a therapeutically effective amount of recombinant arylsulfatase A enzyme.

16 Claims, 12 Drawing Sheets

Specification includes a Sequence Listing.

SEQUENCE LISTING

<160> NUMBER OF SEQ ID NOS: 2

<210> SEQ ID NO 1
<211> LENGTH: 443
<212> TYPE: PRT
<213> ORGANISM: Human

<400> SEQUENCE: 1

```
Pro Val Ser Leu Cys Thr Pro Ser Arg Ala Leu Leu Thr Gly Arg
1               5                   10                  15

Leu Pro Val Arg Met Gly Met Tyr Pro Gly Val Leu Val Pro Ser Ser
                20                  25                  30

Arg Gly Gly Leu Pro Leu Glu Glu Val Thr Val Ala Glu Val Leu Ala
            35                  40                  45

Ala Arg Gly Tyr Leu Thr Gly Met Ala Gly Lys Trp His Leu Gly Val
        50                  55                  60

Gly Pro Glu Gly Ala Phe Leu Pro Pro His Gln Gly Phe His Arg Phe
65                  70                  75                  80

Leu Gly Ile Pro Tyr Ser His Asp Gln Gly Pro Cys Gln Asn Leu Thr
                85                  90                  95

Cys Phe Pro Pro Ala Thr Pro Cys Asp Gly Gly Cys Asp Gln Gly Leu
            100                 105                 110

Val Pro Ile Pro Leu Leu Ala Asn Leu Ser Val Glu Ala Gln Pro Pro
        115                 120                 125

Trp Leu Pro Gly Leu Glu Ala Arg Tyr Met Ala Phe Ala His Asp Leu
    130                 135                 140

Met Ala Asp Ala Gln Arg Gln Asp Arg Pro Phe Phe Leu Tyr Tyr Ala
145                 150                 155                 160

Ser His His Thr His Tyr Pro Gln Phe Ser Gly Gln Ser Phe Ala Glu
                165                 170                 175

Arg Ser Gly Arg Gly Pro Phe Gly Asp Ser Leu Met Glu Leu Asp Ala
            180                 185                 190

Ala Val Gly Thr Leu Met Thr Ala Ile Gly Asp Leu Gly Leu Leu Glu
        195                 200                 205

Glu Thr Leu Val Ile Phe Thr Ala Asp Asn Gly Pro Glu Thr Met Arg
    210                 215                 220

Met Ser Arg Gly Gly Cys Ser Gly Leu Leu Arg Cys Gly Lys Gly Thr
225                 230                 235                 240

Thr Tyr Glu Gly Gly Val Arg Glu Pro Ala Leu Ala Phe Trp Pro Gly
                245                 250                 255

His Ile Ala Pro Gly Val Thr His Glu Leu Ala Ser Ser Leu Asp Leu
            260                 265                 270

Leu Pro Thr Leu Ala Ala Leu Ala Gly Ala Pro Leu Pro Asn Val Thr
        275                 280                 285
```

```
Leu Asp Gly Phe Asp Leu Ser Pro Leu Leu Gly Thr Gly Lys Ser
    290                 295                 300

Pro Arg Gln Ser Leu Phe Phe Tyr Pro Ser Tyr Pro Asp Glu Val Arg
305                 310                 315                 320

Gly Val Phe Ala Val Arg Thr Gly Lys Tyr Lys Ala His Phe Phe Thr
                325                 330                 335

Gln Gly Ser Ala His Ser Asp Thr Thr Ala Asp Pro Ala Cys His Ala
                340                 345                 350

Ser Ser Ser Leu Thr Ala His Glu Pro Pro Leu Leu Tyr Asp Leu Ser
            355                 360                 365

Lys Asp Pro Gly Glu Asn Tyr Asn Leu Leu Gly Val Ala Gly Ala
    370                 375                 380

Thr Pro Glu Val Leu Gln Ala Leu Lys Gln Leu Gln Leu Leu Lys Ala
385                 390                 395                 400

Gln Leu Asp Ala Ala Val Thr Phe Gly Pro Ser Gln Val Ala Arg Gly
                405                 410                 415

Glu Asp Pro Ala Leu Gln Ile Cys Cys His Pro Gly Cys Thr Pro Arg
                420                 425                 430

Pro Ala Cys Cys His Cys Pro Asp Pro His Ala
            435                 440
```

<210> SEQ ID NO 2
<211> LENGTH: 462
<212> TYPE: PRT
<213> ORGANISM: Human

<400> SEQUENCE: 2

```
Thr Pro Asn Leu Asp Gln Leu Ala Ala Gly Gly Leu Arg Phe Thr Asp
1               5                   10                  15

Phe Tyr Val Pro Val Ser Leu Cys Thr Pro Ser Arg Ala Ala Leu Leu
                20                  25                  30

Thr Gly Arg Leu Pro Val Arg Met Gly Met Tyr Pro Gly Val Leu Val
            35                  40                  45

Pro Ser Ser Arg Gly Gly Leu Pro Leu Glu Glu Val Thr Val Ala Glu
    50                  55                  60

Val Leu Ala Ala Arg Gly Tyr Leu Thr Gly Met Ala Gly Lys Trp His
65              70                  75                  80

Leu Gly Val Gly Pro Glu Gly Ala Phe Leu Pro Pro His Gln Gly Phe
                85                  90                  95

His Arg Phe Leu Gly Ile Pro Tyr Ser His Asp Gln Gly Pro Cys Gln
                100                 105                 110

Asn Leu Thr Cys Phe Pro Pro Ala Thr Pro Cys Asp Gly Gly Cys Asp
            115                 120                 125

Gln Gly Leu Val Pro Ile Pro Leu Leu Ala Asn Leu Ser Val Glu Ala
    130                 135                 140

Gln Pro Pro Trp Leu Pro Gly Leu Glu Ala Arg Tyr Met Ala Phe Ala
145                 150                 155                 160

His Asp Leu Met Ala Asp Ala Gln Arg Gln Asp Arg Pro Phe Phe Leu
                165                 170                 175

Tyr Tyr Ala Ser His His Thr His Tyr Pro Gln Phe Ser Gly Gln Ser
                180                 185                 190

Phe Ala Glu Arg Ser Gly Arg Gly Pro Phe Gly Asp Ser Leu Met Glu
            195                 200                 205

Leu Asp Ala Ala Val Gly Thr Leu Met Thr Ala Ile Gly Asp Leu Gly
```

```
                        210                 215                 220
Leu Leu Glu Glu Thr Leu Val Ile Phe Thr Ala Asp Asn Gly Pro Glu
225                 230                 235                 240

Thr Met Arg Met Ser Arg Gly Gly Cys Ser Gly Leu Leu Arg Cys Gly
                245                 250                 255

Lys Gly Thr Thr Tyr Glu Gly Gly Val Arg Glu Pro Ala Leu Ala Phe
                260                 265                 270

Trp Pro Gly His Ile Ala Pro Gly Val Thr His Glu Leu Ala Ser Ser
                275                 280                 285

Leu Asp Leu Leu Pro Thr Leu Ala Ala Leu Ala Gly Ala Pro Leu Pro
                290                 295                 300

Asn Val Thr Leu Asp Gly Phe Asp Leu Ser Pro Leu Leu Leu Gly Thr
305                 310                 315                 320

Gly Lys Ser Pro Arg Gln Ser Leu Phe Phe Tyr Pro Ser Tyr Pro Asp
                325                 330                 335

Glu Val Arg Gly Val Phe Ala Val Arg Thr Gly Lys Tyr Lys Ala His
                340                 345                 350

Phe Phe Thr Gln Gly Ser Ala His Ser Asp Thr Thr Ala Asp Pro Ala
                355                 360                 365

Cys His Ala Ser Ser Ser Leu Thr Ala His Glu Pro Pro Leu Leu Tyr
                370                 375                 380

Asp Leu Ser Lys Asp Pro Gly Glu Asn Tyr Asn Leu Leu Gly Gly Val
385                 390                 395                 400

Ala Gly Ala Thr Pro Glu Val Leu Gln Ala Leu Lys Gln Leu Gln Leu
                405                 410                 415

Leu Lys Ala Gln Leu Asp Ala Ala Val Thr Phe Gly Pro Ser Gln Val
                420                 425                 430

Ala Arg Gly Glu Asp Pro Ala Leu Gln Ile Cys Cys His Pro Gly Cys
                435                 440                 445

Thr Pro Arg Pro Ala Cys Cys His Cys Pro Asp Pro His Ala
450                 455                 460
```

METHODS AND COMPOSITIONS FOR CNS DELIVERY OF ARYLSULFATASE A

CROSS REFERENCE TO RELATED APPLICATIONS

This application claims priority to U.S. Provisional Application 62/296,563 filed Feb. 17, 2016 and U.S. Provisional Application 62/453,864 filed Feb. 2, 2017; which are hereby incorporated by reference in their entireties.

SEQUENCE LISTING

The instant application contains a Sequence Listing which has been submitted electronically and is hereby incorporated by reference in its entirety. The file named "SHR-1096_SequenceListing_ST25.txt" was created on Jan. 9, 2020 and is 8,090 bytes in size.

BACKGROUND

Enzyme replacement therapy (ERT) involves the systemic administration of natural or recombinantly-derived proteins and/or enzymes to a subject. Approved therapies are typically administered to subjects intravenously and are generally effective in treating the somatic symptoms of the underlying enzyme deficiency. As a result of the limited distribution of the intravenously administered protein and/or enzyme into the cells and tissues of the central nervous system (CNS), the treatment of diseases having a CNS etiology has been especially challenging because the intravenously administered proteins and/or enzymes do not adequately cross the blood-brain barrier (BBB).

The blood-brain barrier (BBB) is a structural system comprised of endothelial cells that functions to protect the central nervous system (CNS) from deleterious substances in the blood stream, such as bacteria, macromolecules (e.g., proteins) and other hydrophilic molecules, by limiting the diffusion of such substances across the BBB and into the underlying cerebrospinal fluid (CSF) and CNS.

There are several ways of circumventing the BBB to enhance brain delivery of a therapeutic agent including direct intra-cranial injection, transient permeabilization of the BBB, and modification of the active agent to alter tissue distribution. Direct injection of a therapeutic agent into brain tissue bypasses the vasculature completely, but suffers primarily from the risk of complications (infection, tissue damage, immune responsive) incurred by intra-cranial injections and poor diffusion of the active agent from the site of administration. To date, direct administration of proteins into the brain substance has not achieved significant therapeutic effect due to diffusion barriers and the limited volume of therapeutic that can be administered. Convection-assisted diffusion has been studied via catheters placed in the brain parenchyma using slow, long-term infusions (Bobo, et al., Proc. Natl. Acad. Sci. U.S.A 91, 2076-2080 (1994); Nguyen, et al. J. Neurosurg. 98, 584-590 (2003)), but no approved therapies currently use this approach for long-term therapy. In addition, the placement of intracerebral catheters is very invasive and less desirable as a clinical alternative.

Intrathecal (IT) injection, or the administration of proteins to the cerebrospinal fluid (CSF), has also been attempted but has not yet yielded therapeutic success. A major challenge in this treatment has been the tendency of the active agent to bind the ependymal lining of the ventricle very tightly which prevented subsequent diffusion. Currently, there are no approved products for the treatment of brain genetic disease by administration directly to the CSF.

In fact, many believed that the barrier to diffusion at the brain's surface, as well as the lack of effective and convenient delivery methods, were too great an obstacle to achieve adequate therapeutic effect in the brain for any disease.

Many lysosomal storage disorders affect the nervous system and thus demonstrate unique challenges in treating these diseases with traditional therapies. There is often a large build-up of glycosaminoglycans (GAGs) in neurons and meninges of affected individuals, leading to various forms of CNS symptoms. To date, no CNS symptoms resulting from a lysosomal disorder has successfully been treated by any means available.

Thus, there remains a great need to effectively deliver therapeutic agents to the brain. More particularly, there is a great need for more effective delivery of active agents to the central nervous system for the treatment of lysosomal storage disorders.

SUMMARY OF THE INVENTION

The present invention provides, among other things, compositions and methods for treating metachromatic leukodystrophy (MLD) Syndrome by intrathecal delivery of arylsulfatase A.

In certain embodiments, provided are methods of treating metachromatic leukodystrophy (MLD) Syndrome comprising a step of administering intrathecally to a subject in need of treatment a recombinant arylsulfatase A (ASA) enzyme at a therapeutically effective dose and an administration interval for a treatment period sufficient to improve, stabilize or reduce decline of one or more motor functions relative to baseline.

In some embodiments, administering of the recombinant ASA enzyme further results in improvement, stabilization or reduction decline of one or more cognitive, adaptive, and/or executive functions.

In some embodiments, the one or more motor functions comprises gross motor function. In some embodiments, the gross motor function is assessed by a Gross Motor Function Measure (GMFM) test such as, for example, GMFM-88. In some embodiments, the baseline GMFM-88 score of the subject is greater than 40%. In some embodiments, the baseline GMFM-88 score of the patient is less than 40%. In some embodiments, administering of the recombinant ASA enzyme results in decline of the GMFM-88 score of less than 10%, 20%, 30%, 40%, or 50%. In some embodiments, the administering of the recombinant ASA enzyme results in substantial stabilization of the GMFM-88 score. In some embodiments, administering of the recombinant ASA enzyme results in improvement of the GMFM-88 score.

In certain embodiments, provided are methods of treating metachromatic leukodystrophy (MLD) Syndrome comprising a step of administering intrathecally to a subject in need of treatment a recombinant arylsulfatase A (ASA) enzyme at a therapeutically effective dose and an administration interval for a treatment period sufficient to decrease levels of a biomarker that accumulates in MLD in a bodily fluid selected from the group consisting of cerebrospinal fluid, urine, blood, and blood serum relative to a baseline level of the biomarker. In some embodiments, the biomarker is selected from the group consisting of sulfatide, lysosulfatide, and combinations thereof. In some embodiments, the biomarker is sulfatide. In some embodiments, the bodily fluid is cerebrospinal fluid.

In some embodiments, the baseline sulfatide level in the cerebrospinal fluid is greater than about 0.1 µg/mL. In some embodiments, the baseline sulfatide level in the cerebrospinal fluid is greater than about 0.2 µg/mL. In some embodiments, the baseline sulfatide level in the cerebrospinal fluid is greater than about 0.3 µg/mL.

In some embodiments, the administering of the recombinant ASA enzyme results in reduction of sulfatide levels in the cerebrospinal fluid by more than about 0.1 µg/mL. In some embodiments, the administering of the recombinant ASA enzyme results in reduction of sulfatide levels in the cerebrospinal fluid by more than about 0.2 µg/mL.

In certain embodiments, provided are methods of treating metachromatic leukodystrophy (MLD) Syndrome comprising a step of administering intrathecally to a subject in need of treatment a recombinant arylsulfatase A (ASA) enzyme at a therapeutically effective dose and an administration interval for a treatment period sufficient to increase levels of a biomarker that is decreased in MLD in a brain tissue relative to a baseline level of the biomarker.

In some embodiments, the brain tissue is the deep white matter of the brain. In some embodiments, the biomarker is a metabolite, such as, for example, N-acetylaspartate. In some embodiments, levels of N-acetylaspartate are assessed by proton magnetic resonance spectroscopy.

In certain embodiments, provided are methods of treating metachromatic leukodystrophy (MLD) Syndrome comprising a step of administering intrathecally to a subject in need of treatment a recombinant arylsulfatase A enzyme at a therapeutically effective dose and an administration interval for a treatment period sufficient to stabilize or reduce brain lesion involvement relative to baseline.

In some embodiments, brain lesion involvement is assessed by the MLD MRI (Magnetic Resonance Imaging) severity score. In some embodiments, administering of the recombinant ASA enzyme results in reduction of the MLD MRI severity score in the subject relative to baseline. In some embodiments, administering of the recombinant ASA enzyme results in stabilization of the MLD MRI severity score in the subject relative to baseline.

In some embodiments, the therapeutically effective dose is or is greater than 10 mg. In some embodiments, the therapeutically effective dose is or is greater than 30 mg. In some embodiments, the therapeutically effective dose is or is greater than 100 mg. In some embodiments, the therapeutically effective dose is less than 200 mg.

In some embodiments, the administration interval is once a week. In some embodiments, the administration interval is once every two weeks. In some embodiments, the administration interval is once a month.

In some embodiments, the subject is a mammal. In some embodiments, the subject is human.

In some embodiments, the subject is sixteen years old or younger. In some embodiments, the subject is twelve years old or younger. In some embodiments, the subject is nine years old or younger. In some embodiments, the subject is six years old or younger. In some embodiments, the subject is four years old or younger. In some embodiments, the subject is three years old or younger. In some embodiments, the subject is two years old or younger. In some embodiments, the subject is 18 months or younger. In some embodiments, the subject is 12 months or younger.

In some embodiments, the subject is 6 months or younger.

In some embodiments, the subject has exhibited at least one symptom of metachromatic leukodystrophy. In some embodiments, the subject has not exhibited any symptoms of metachromatic leukodystrophy. In some embodiments, the subject has been diagnosed with metachromatic leukodystrophy. In some embodiments, the subject has been identified as being at risk of developing metachromatic leukodystrophy.

In some embodiments, the arylsulfatase A is administered into the spinal canal. In some embodiments, the arylsulfatase A is administered into the lumbar region. In some embodiments, the arylsulfatase A is administered through lumbar puncture.

In some embodiments, the intrathecal administration is through intermittent or continuous access to an implanted intrathecal drug delivery device (IDDD).

In some embodiments, the treatment period is at least 6 months. In some embodiments, the treatment period is at least 9 months. In some embodiments, the treatment period is at least 12 months. In some embodiments, the treatment period is at least 24 months. In some embodiments, the treatment period is at least 26 months.

In some embodiments, no serious adverse effects associated with administration of the recombinant arylsulfatase A are observed in the subject.

In certain embodiments, provided are recombinant arylsulfatase A (ASA) enzymes for use in a method comprising a step of: administering intrathecally to a subject who is at risk of or suffering from metachromatic leukodystrophy the recombinant arylsulfatase A enzyme at a therapeutically effective dose and an administration interval for a treatment period sufficient to improve, stabilize or reduce decline of one or more motor functions relative to a baseline.

In certain embodiments, provided are recombinant arylsulfatase A (ASA) enzymes for use in a method comprising a step of: administering intrathecally to a subject who is at risk of or suffering from metachromatic leukodystrophy the recombinant arylsulfatase A enzyme at a therapeutically effective dose and an administration interval for a treatment period sufficient to decrease sulfatide levels in the cerebrospinal fluid (CSF) relative to baseline.

In certain embodiments, provided are recombinant arylsulfatase A (ASA) enzymes for use in a method comprising a step of: administering intrathecally to a subject who is at risk of or suffering from metachromatic leukodystrophy the recombinant arylsulfatase A enzyme at a therapeutically effective dose and an administration interval for a treatment period sufficient to stabilize or reduce brain lesion involvement relative to baseline.

In certain embodiments, provided are uses of recombinant arylsulfatase A enzymes in the manufacture of a medicament for treating or preventing metachromatic leukodystrophy, wherein the treatment comprises a step of: administering intrathecally to a subject at risk of or suffering from metachromatic leukodystrophy the recombinant arylsulfatase A enzyme at a therapeutically effective dose and an administration interval for a treatment period sufficient to improve, stabilize, or reduce decline of one or more motor functions relative to a baseline.

In certain embodiments, provided are uses of recombinant arylsulfatase A enzymes in the manufacture of a medicament for treating or preventing metachromatic leukodystrophy, wherein the treatment comprises a step of: administering intrathecally to a subject at risk of or suffering from metachromatic leukodystrophy the recombinant arylsulfatase A enzyme at a therapeutically effective dose and an administration interval for a treatment period sufficient to decrease sulfatide levels in the cerebrospinal fluid (CSF) relative to baseline.

In certain embodiments, provided are uses of recombinant arylsulfatase A enzymes in the manufacture of a medicament for treating or preventing metachromatic leukodystrophy, wherein the treatment comprises a step of: administering intrathecally to a subject at risk of or suffering from metachromatic leukodystrophy the recombinant arylsulfatase A enzyme at a therapeutically effective dose and an administration interval for a treatment period sufficient to stabilize or reduce brain lesion involvement relative to baseline.

In some embodiments, recombinant ASA enzymes comprises an amino acid sequence that is at least 85% identical at the amino acid level to SEQ ID NO: 1. In some embodiments, recombinant ASA enzymes comprise an amino acid sequence that is at least 90% identical at the amino acid level to SEQ ID NO: 1. In some embodiments, recombinant ASA enzymes comprise an amino acid sequence that is at least 95% identical at the amino acid level to SEQ ID NO: 1.

In some embodiments, recombinant ASA enzymes comprise an amino acid sequence that is at least 98% identical at the amino acid level to SEQ ID NO: 1. In some embodiments, recombinant ASA enzymes comprise an amino acid sequence of SEQ ID NO: 1.

In some embodiments, recombinant ASA enzymes comprise an amino acid sequence that contains no more than four mismatches with that of SEQ ID NO: 1. In some embodiments, recombinant ASA enzymes comprise an amino acid sequence that contains no more than three mismatches with that of SEQ ID NO: 1. In some embodiments, recombinant ASA enzymes comprise an amino acid sequence that contains no more than two mismatches with that of SEQ ID NO: 1.

In some embodiments, recombinant ASA enzymes comprise an amino acid sequence that contains no more than one mismatch with that of SEQ ID NO: 1.

BRIEF DESCRIPTION OF THE DRAWINGS

FIG. 9A shows the mean GMFM-88 total scores for each cohort by study visit. FIG. 9B shows individual GMFM-88 total scores by patient age over 104 weeks of treatment.

DEFINITIONS

Figure 1:
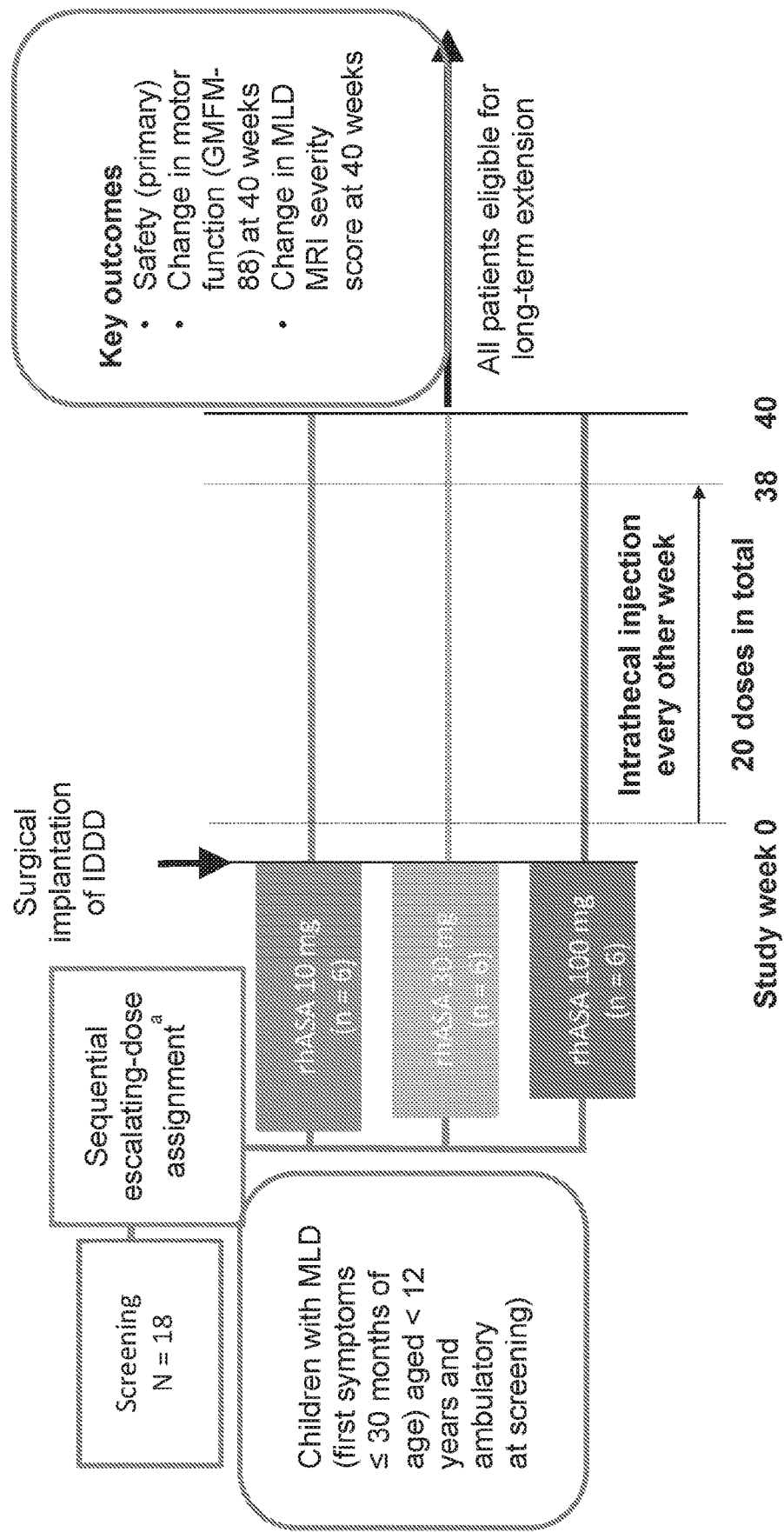
FIG. 1 illustrates the design of a phase 1/2, non-randomized, open-label, 40-week, dose-escalation clinical study of intrathecally delivered recombinant human arylsulfatase A in children with Metachromatic Leukodystrophy (MLD). IDDD: intrathecal drug delivery device; rhASA: recombinant human arylsulfatase A.

In order for the present invention to be more readily understood, certain terms are first defined below. Additional definitions for the following terms and other terms are set forth throughout the specification.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Amelioration: As used herein, the term "amelioration" is meant the prevention, reduction or palliation of a state, or improvement of the state of a subject. Amelioration includes, but does not require complete recovery or complete prevention of a disease condition. In some embodiments, amelioration includes increasing levels of relevant protein or its activity that is deficient in relevant disease tissues.

Baseline: As used herein, the term "baseline" refers to the value, level, status, condition, etc. before a treatment period begins, typically at the beginning of treatment.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Bulking agent: As used herein, the term "bulking agent" refers to a compound which adds mass to the lyophilized mixture and contributes to the physical structure of the lyophilized cake (e.g., facilitates the production of an essentially uniform lyophilized cake which maintains an open pore structure). Exemplary bulking agents include mannitol, glycine, sodium chloride, hydroxyethyl starch, lactose, sucrose, trehalose, polyethylene glycol and dextran.

Cation-independent mannose-6-phosphate receptor (CI-MPR): As used herein, the term "cation-independent mannose-6-phosphate receptor (CI-MPR)" refers to a cellular receptor that binds mannose-6-phosphate (M6P) tags on acid hydrolase precursors in the Golgi apparatus that are destined for transport to the lysosome. In addition to mannose-6-phosphates, the CI-MPR also binds other proteins including IGF-II. The CI-MPR is also known as "M6P/IGF-II receptor," "CI-MPR/IGF-II receptor," "IGF-II receptor" or "IGF2 Receptor." These terms and abbreviations thereof are used interchangeably herein.

Concurrent immunosuppressant therapy: As used herein, the term "concurrent immunosuppressant therapy" includes any immunosuppressant therapy used as pre-treatment, pre-conditioning or in parallel to a treatment method.

Diluent: As used herein, the term "diluent" refers to a pharmaceutically acceptable (e.g., safe and non-toxic for administration to a human) diluting substance useful for the preparation of a reconstituted formulation. Exemplary diluents include sterile water, bacteriostatic water for injection (BWFI), a pH buffered solution (e.g. phosphate-buffered saline), sterile saline solution, Ringer's solution or dextrose solution.

Dosage form: As used herein, the terms "dosage form" and "unit dosage form" refer to a physically discrete unit of a therapeutic protein for the patient to be treated. Each unit contains a predetermined quantity of active material calculated to produce the desired therapeutic effect. It will be understood, however, that the total dosage of the composition will be decided by the attending physician within the scope of sound medical judgment.

Enzyme replacement therapy (ERT): As used herein, the term "enzyme replacement therapy (ERT)" refers to any therapeutic strategy that corrects an enzyme deficiency by providing the missing enzyme. In some embodiments, the missing enzyme is provided by intrathecal administration. In some embodiments, the missing enzyme is provided by infusing into bloodstream. Once administered, enzyme is taken up by cells and transported to the lysosome, where the enzyme acts to eliminate material that has accumulated in the lysosomes due to the enzyme deficiency. Typically, for lysosomal enzyme replacement therapy to be effective, the therapeutic enzyme is delivered to lysosomes in the appropriate cells in target tissues where the storage defect is manifest.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of lysosomal storage disease as the individual being treated, who is about the same age as the individual being treated (to ensure that the stages of the disease in the treated individual and the control individual(s) are comparable).

Individual, subject, patient: As used herein, the terms "subject," "individual" or "patient" refer to a human or a non-human mammalian subject. The individual (also referred to as "patient" or "subject") being treated is an individual (fetus, infant, child, adolescent, or adult human) suffering from a disease.

Intrathecal administration: As used herein, the term "intrathecal administration" or "intrathecal injection" refers to an injection into the spinal canal (intrathecal space surrounding the spinal cord). Various techniques may be used including lumbar puncture. In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between the third and fourth lumbar (lower back) vertebrae and, more inclusively, the L2-S1 region of the spine.

Linker: As used herein, the term "linker" refers to, in a fusion protein, an amino acid sequence other than that appearing at a particular position in the natural protein and is generally designed to be flexible or to interpose a structure, such as an a-helix, between two protein moieties. A linker is also referred to as a spacer.

Lyoprotectant: As used herein, the term "lyoprotectant" refers to a molecule that prevents or reduces chemical and/or physical instability of a protein or other substance upon lyophilization and subsequent storage. Exemplary lyoprotectants include sugars such as sucrose or trehalose; an amino acid such as monosodium glutamate or histidine; a methylamine such as betaine; a lyotropic salt such as magnesium sulfate: a polyol such as trihydric or higher sugar alcohols, e.g. glycerin, erythritol, glycerol, arabitol, xylitol, sorbitol, and mannitol; propylene glycol; polyethylene glycol; Pluronics; and combinations thereof. In some embodiments, a lyoprotectant is a non-reducing sugar, such as trehalose or sucrose.

Lysosomal enzyme: As used herein, the term "lysosomal enzyme" refers to any enzyme that is capable of reducing accumulated materials in mammalian lysosomes or that can rescue or ameliorate one or more lysosomal storage disease symptoms. Lysosomal enzymes suitable for the invention include both wild-type or modified lysosomal enzymes and can be produced using recombinant and synthetic methods or purified from nature sources. Exemplary lysosomal enzymes are listed in Table 1.

Lysosomal enzyme deficiency: As used herein, "lysosomal enzyme deficiency" refers to a group of genetic disorders that result from deficiency in at least one of the enzymes that are required to break macromolecules (e.g., enzyme substrates) down to peptides, amino acids, monosaccharides, nucleic acids and fatty acids in lysosomes. As a result, individuals suffering from lysosomal enzyme deficiencies have accumulated materials in various tissues (e.g., CNS, liver, spleen, gut, blood vessel walls and other organs).

Lysosomal Storage Disease: As used herein, the term "lysosomal storage disease" refers to any disease resulting from the deficiency of one or more lysosomal enzymes necessary for metabolizing natural macromolecules. These diseases typically result in the accumulation of un-degraded molecules in the lysosomes, resulting in increased numbers of storage granules (also termed storage vesicles). These diseases and various examples are described in more detail below.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Replacement enzyme: As used herein, the term "replacement enzyme" refers to any enzyme that can act to replace at least in part the deficient or missing enzyme in a disease to be treated. In some embodiments, the term "replacement enzyme" refers to any enzyme that can act to replace at least in part the deficient or missing lysosomal enzyme in a lysosomal storage disease to be treated. In some embodiments, a replacement enzyme is capable of reducing accumulated materials in mammalian lysosomes or that can rescue or ameliorate one or more lysosomal storage disease symptoms. Replacement enzymes suitable for the invention include both wild-type or modified lysosomal enzymes and can be produced using recombinant and synthetic methods or purified from nature sources. A replacement enzyme can be a recombinant, synthetic, gene-activated or natural enzyme.

Soluble: As used herein, the term "soluble" refers to the ability of a therapeutic agent to form a homogenous solution. In some embodiments, the solubility of the therapeutic agent in the solution into which it is administered and by which it is transported to the target site of action (e.g., the cells and tissues of the brain) is sufficient to permit the delivery of a therapeutically effective amount of the therapeutic agent to the targeted site of action. Several factors can impact the solubility of the therapeutic agents. For example, relevant factors which may impact protein solubility include ionic strength, amino acid sequence and the presence of other co-solubilizing agents or salts (e.g., calcium salts). In some embodiments, the pharmaceutical compositions are formulated such that calcium salts are excluded from such compositions. In some embodiments, therapeutic agents in accordance with the present invention are soluble in its corresponding pharmaceutical composition. It will be appreciated that, while isotonic solutions are generally preferred for parenterally administered drugs, the use of isotonic solutions may limit adequate solubility for some therapeutic agents and, in particular some proteins and/or enzymes. Slightly hypertonic solutions (e.g., up to 175 mM sodium chloride in 5 mM sodium phosphate at pH 7.0) and sugar-containing solutions (e.g., up to 2% sucrose in 5 mM sodium phosphate at pH 7.0) have been demonstrated to be well tolerated in monkeys. For example, the most common approved CNS bolus formulation composition is saline (150 mM NaCl in water).

Stability: As used herein, the term "stable" refers to the ability of the therapeutic agent (e.g., a recombinant enzyme) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In general, pharmaceutical compositions described herein have been formulated such that they are capable of stabilizing, or alternatively slowing or preventing the degradation, of one or more therapeutic agents formulated therewith (e.g., recombinant proteins). In the context of a formulation a stable formulation is one in which the therapeutic agent therein essentially retains its physical and/or chemical integrity and biological activity upon storage and during processes (such as freeze/thaw, mechanical mixing and lyophilization). For protein stability, it can be measure by formation of high molecular weight (HMW) aggregates, loss of enzyme activity, generation of peptide fragments and shift of charge profiles.

Subject: As used herein, the term "subject" means any mammal, including humans. In certain embodiments of the present invention the subject is an adult, an adolescent, a child, or an infant. Also contemplated by the present invention are the administration of the pharmaceutical compositions and/or performance of the methods of treatment in-utero.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Synthetic CSF: As used herein, the term "synthetic CSF" refers to a solution that has pH, electrolyte composition, glucose content and osmolarity consistent with the cerebrospinal fluid. Synthetic CSF is also referred to as artificial CSF. In some embodiments, synthetic CSF is an Elliott's B solution.

Suitable for CNS delivery: As used herein, the phrase "suitable for CNS delivery" or "suitable for intrathecal delivery" as it relates to the pharmaceutical compositions of the present invention generally refers to the stability, tolerability, and solubility properties of such compositions, as well as the ability of such compositions to deliver an effective amount of the therapeutic agent contained therein to the targeted site of delivery (e.g., the CSF or the brain).

Target tissues: As used herein, the term "target tissues" refers to any tissue that is affected by the lysosomal storage disease to be treated or any tissue in which the deficient lysosomal enzyme is normally expressed. In some embodiments, target tissues include those tissues in which there is a detectable or abnormally high amount of enzyme substrate, for example stored in the cellular lysosomes of the tissue, in patients suffering from or susceptible to the lysosomal storage disease. In some embodiments, target tissues include those tissues that display disease-associated pathology, symptom, or feature. In some embodiments, target tissues include those tissues in which the deficient lysosomal enzyme is normally expressed at an elevated level. As used herein, a target tissue may be a brain target tissue, a spinal cord target tissue and/or a peripheral target tissue. Exemplary target tissues are described in detail below.

Therapeutic moiety: As used herein, the term "therapeutic moiety" refers to a portion of a molecule that renders the therapeutic effect of the molecule. In some embodiments, a therapeutic moiety is a polypeptide having therapeutic activity.

Therapeutically effective amount: As used herein, the term "therapeutically effective amount" refers to an amount of a therapeutic protein (e.g., replacement enzyme) which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Tolerable: As used herein, the terms "tolerable" and "tolerability" refer to the ability of the pharmaceutical compositions of the present invention to not elicit an adverse reaction in the subject to whom such composition is administered, or alternatively not to elicit a serious adverse reaction in the subject to whom such composition is administered. In some embodiments, the pharmaceutical compositions of the present invention are well tolerated by the subject to whom such compositions is administered.

Treatment: As used herein, the term "treatment" (also "treat" or "treating") refers to any administration of a therapeutic protein (e.g., lysosomal enzyme) that partially or completely alleviates, ameliorates, relieves, inhibits, delays onset of, reduces severity of and/or reduces incidence of one or more symptoms or features of a particular disease, disorder, and/or condition (e.g., metachromatic leukodystrophy). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

DETAILED DESCRIPTION OF THE INVENTION

The present invention provides, among other things, improved methods and compositions for effective direct delivery of a therapeutic agent to the central nervous system (CNS). The present invention is based on unexpected discovery that a replacement enzyme (e.g., an ASA protein) for a lysososmal storage disease (e.g., Metachromatic Leukodystrophy Disease) can be directly introduced into the cerebrospinal fluid (CSF) of a subject in need of treatment at a high concentration without inducing substantial adverse effects in the subject. More surprisingly, the present inventors found that the replacement enzyme may be delivered in a simple saline or buffer-based formulation, without using synthetic CSF. Even more unexpectedly, intrathecal delivery according to the present invention does not result in substantial adverse effects, such as severe immune response, in the subject. Therefore, in some embodiments, intrathecal delivery according to the present invention may be used in absence of concurrent immunosuppressant therapy (e.g., without induction of immune tolerance by pre-treatment or pre-conditioning).

In some embodiments, intrathecal delivery according to the present invention permits efficient diffusion across various brain tissues resulting in effective delivery of the replacement enzyme in various target brain tissues in surface, shallow and/or deep brain regions. In some embodiments, intrathecal delivery according to the present invention resulted in sufficient amount of replacement enzymes entering the peripheral circulation. As a result, in some cases, intrathecal delivery according to the present invention resulted in delivery of the replacement enzyme in peripheral tissues, such as liver, heart, spleen and kidney. This discovery is unexpected and can be particular useful for the treatment of lysosomal storage diseases that have both CNS and peripheral components, which would typically require both regular intrathecal administration and intravenous administration. It is contemplated that intrathecal delivery according to the present invention may allow reduced dosing and/or frequency of iv injection without compromising therapeutic effects in treating peripheral symptoms.

The present invention provides various unexpected and beneficial features that allow efficient and convenient delivery of replacement enzymes to various brain target tissues, resulting in effective treatment of lysosomal storage diseases that have CNS indications.

Various aspects of the invention are described in detail in the following sections. The use of sections is not meant to limit the invention. Each section can apply to any aspect of the invention. In this application, the use of "or" means "and/or" unless stated otherwise.

Recombinant Arylsulfatase A Enzymes

In some embodiments, inventive methods and compositions provided by the present invention are used to deliver a recombinant arylsulfatase A (ASA) enzyme to the CNS for treatment of Metachromatic Leukodystrophy Disease. A suitable ASA enzyme can be any molecule or a portion of a molecule that can substitute for naturally-occurring arylsulfatase A (ASA) enzyme activity or rescue one or more phenotypes or symptoms associated with ASA-deficiency. In some embodiments, a replacement enzyme suitable for the invention is a polypeptide having an N-terminus and a C-terminus and an amino acid sequence substantially similar or identical to mature human ASA enzyme.

Typically, human ASA is produced as a precursor molecule that is processed to a mature form. This process generally occurs by removing the 18 amino acid signal peptide. Typically, the precursor form is also referred to as full-length precursor or full-length ASA enzyme, which contains 507 amino acids. The N-terminal 18 amino acids are cleaved, resulting in a mature form that is 489 amino acids in length. Thus, it is contemplated that the N-terminal 18 amino acids is generally not required for the ASA enzyme activity. The amino acid sequences of the mature form (SEQ ID NO: 1) and full-length precursor (SEQ ID NO: 2) of a typical wild-type or naturally-occurring human ASA enzyme are shown in Table 1.

TABLE 1

| Human ASA | Sequence |
| --- | --- |
| Mature Form | RPPNIVLIFADDLGYGDLGCYGHPSSTTPNLDQLAAGGLRFTDFYV<br>PVSLCTPSRAALLTGRLPVRMGMYPGVLVPSSRGGLPLEEVTVAE<br>VLAARGYLTGMAGKWHLGVGPEGAFLPPHQGFHRFLGIPYSHDQ<br>GPCQNLTCFPPATPCDGGCDQGLVPIPLLANLSVEAQPPWLPGLEA<br>RYMAFAHDLMADAQRQDRPFFLYYASHHTHYPQFSGQSFAERSG<br>RGPFGDSLMELDAAVGTLMTAIGDLGLLEETLVIFTADNGPETMR<br>MSRGGCSGLLRCGKGTTYEGGVREPALAFVVPGHIAPGVTHELASS<br>LDLLPTLAALAGAPLPNVTLDGFDLSPLLLGTGKSPRQSLFFYPSYP<br>DEVRGVFAVRTGKYKAHFFTQGSAHSDTTADPACHASSSLTAHEP<br>PLLYDLSKDPGENYNLLGGVAGATPEVLQALKQLQLLKAQLDAA<br>VTFGPSQVARGEDPALQICCHPGCTPRPACCHCPDPHA (SEQ ID NO: 1) |
| Full-Length<br>Precursor | MGAPRSLLLALAAGLAVARPPNIVLIFADDLGYGDLGCYGHPSST<br>TPNLDQLAAGGLRFTDFYVPVSLCTPSRAALLTGRLPVRMGMYPG<br>VLVPSSRGGLPLEEVTVAEVLAARGYLTGMAGKWHLGVGPEGAF<br>LPPHQGFHRFLGIPYSHDQGPCQNLTCFPPATPCDGGCDQGLVPIP<br>LLANLSVEAQPPWLPGLEARYMAFAHDLMADAQRQDRPFFLYYA<br>SHHTHYPQFSGQSFAERSGRGPFGDSLMELDAAVGTLMTAIGDLG<br>LLEETLVIFTADNGPETMRMSRGGCSGLLRCGKGTTYEGGVREPA<br>LAFWPGHIAPGVTHELASSLDLLPTLAALAGAPLPNVTLDGFDLSP<br>LLLGTGKSPRQSLFFYPSYPDEVRGVFAVRTGKYKAHFFTQGSAH<br>SDTTADPACHASSSLTAHEPPLLYDLSKDPGENYNLLGGVAGATP<br>EVLQALKQLQLLKAQLDAAVTFGPSQVARGEDPALQICCHPGCTP<br>RPACCHCPDPHA (SEQ ID NO: 2) |

Thus, in some embodiments, a recombinant arylsulfatase A in the present invention is mature human ASA protein (SEQ ID NO:1). In some embodiments, a suitable recombinant arylsulfatase A may be a homologue or an analogue of mature human ASA protein. For example, a homologue or an analogue of mature human ASA protein may be a modified mature human ASA protein containing one or more amino acid substitutions, deletions, and/or insertions as compared to a wild-type or naturally-occurring ASA protein (e.g., SEQ ID NO:1), while retaining substantial ASA protein activity. Thus, in some embodiments, a recombinant arylsulfatase A suitable for the present invention is substantially homologous to mature human ASA protein (SEQ ID NO:1). In some embodiments, a recombinant arylsulfatase A suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, a recombinant arylsulfatase A suitable for the present invention is substantially identical to mature human ASA protein (SEQ ID NO:1). In some embodiments, a recombinant arylsulfatase A suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1. For example, in some embodiments, a recombinant arylsulfatase A enzyme comprises an amino acid sequence that is at least 85% identical at the amino acid level to SEQ ID NO: 1. In some embodiments, a recombinant ASA enzyme comprises an amino acid sequence that is at least 90% identical at the amino acid level to SEQ ID NO: 1. In some embodiments, a recombinant arylsulfatase A enzyme comprises an amino acid sequence that is at least 95% identical at the amino acid level to SEQ ID NO: 1. In some embodiments, a recombinant arylsulfatase A enzyme comprises an amino acid sequence that is at least 98% identical at the amino acid level to SEQ ID NO: 1. In some embodiments, a recombinant arylsulfatase A enzyme comprises an amino acid sequence an amino acid sequence of SEQ ID NO: 1.

In some embodiments, a recombinant arylsulfatase A enzyme comprises an amino acid sequence that has a few mismatches with that of SEQ ID NO: 1, for example no more than four, no more than three, no more than two, or no more than one mismatch with that of SEQ ID NO: 1.

In some embodiments, a recombinant arylsulfatase A suitable for the present invention contains a fragment or a portion of mature human ASA protein. In some embodiments, the fragment or portion is catalytically active.

Additionally or alternatively, a replacement enzyme suitable for the present invention is full-length ASA protein. In some embodiments, a suitable replacement enzyme may be a homologue or an analogue of full-length human ASA protein. For example, a homologue or an analogue of full-length human ASA protein may be a modified full-length human ASA protein containing one or more amino acid substitutions, deletions, and/or insertions as compared to a wild-type or naturally-occurring full-length ASA protein (e.g., SEQ ID NO:2), while retaining substantial ASA protein activity. Thus, in some embodiments, a replacement enzyme suitable for the present invention is substantially homologous to full-length human ASA protein (SEQ ID NO:2). In some embodiments, a replacement enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:2. In some embodiments, a replacement enzyme suitable for the present invention is substantially identical to SEQ ID NO:2. In some embodiments, a replacement enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:2. In some embodiments, a replacement enzyme suitable for the present invention contains a fragment or a portion of full-length human ASA protein. As used herein, a full-length ASA protein typically contains signal peptide sequence.

In some embodiments, a recombinant arylsulfatase A enzyme includes a targeting moiety (e.g., a lysosome targeting sequence) and/or a membrane-penetrating peptide. In some embodiments, a targeting sequence and/or a membrane-penetrating peptide is an intrinsic part of the recombinant arylsulfatase A (e.g., via a chemical linkage, via a fusion protein). In some embodiments, a targeting sequence contains a mannose-6-phosphate moiety. In some embodiments, a targeting sequence contains an IGF-I moiety. In some embodiments, a targeting sequence contains an IGF-II moiety.

In some embodiments, a recombinant arylsulfatase A enzyme suitable for the invention may have a wild-type or naturally occurring sequence. In some embodiments, a recombinant arylsulfatase A enzyme suitable for the invention may have a modified sequence having substantial homology or identify to the wild-type or naturally-occurring sequence (e.g., having at least 50%, 55%, 60%, 65%, 70%, 75%, 80%, 85%, 90%, 95%, 98% sequence identity to the wild-type or naturally-occurring sequence).

Replacement enzymes (e.g., recombinant arylsulfatase A enzyme) suitable for the present invention may be recombinantly produced, for example, by utilizing a host cell system engineered to express a nucleic acid encoding the recombinant enzyme. Alternatively or additionally, replacement enzymes may be partially or fully prepared by chemical synthesis.

When a replacement enzyme is recombinantly produced, any expression system can be used. To give but a few examples, known expression systems include, for example, egg, baculovirus, insect, plant, yeast, or mammalian cells.

In some embodiments, enzymes suitable for the present invention are produced in mammalian cells. Non-limiting examples of mammalian cells that may be used in accordance with the present invention include BALB/c mouse myeloma line (NSO/l, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol, 36:59, 1977); human fibrosarcoma cell line (e.g., HT1080); baby hamster kidney cells (BHK, ATCC CCL 10); Chinese hamster ovary cells +/− DHFR (CHO, Urlaub and Chasin, Proc. Natl. Acad. Sci. USA, 77:4216, 1980); mouse sertoli cells (TM4, Mather, Biol. Reprod, 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

In some embodiments, inventive methods according to the present invention are used to deliver replacement enzymes produced from human cells. In some embodiments, inventive methods according to the present invention are used to deliver replacement enzymes produced from CHO cells.

In some embodiments, replacement enzymes delivered using a method of the invention contain a moiety that binds to a receptor on the surface of brain cells to facilitate cellular uptake and/or lysosomal targeting. For example, such a receptor may be the cation-independent mannose-6-phosphate receptor (CI-MPR) which binds the mannose-6-phosphate (M6P) residues. In addition, the CI-MPR also binds other proteins including IGF-II. In some embodiments, a replacement enzyme suitable for the present invention contains M6P residues on the surface of the protein. In some embodiments, a replacement enzyme suitable for the present invention may contain bis-phosphorylated oligosaccharides which have higher binding affinity to the CI-MPR. In some embodiments, a suitable enzyme contains up to about an average of about at least 20% bis-phosphorylated oligosaccharides per enzyme. In other embodiments, a suitable enzyme may contain about 10%, 15%, 18%, 20%, 25%, 30%, 35%, 40%, 45%, 50%, 55%, 60% bis-phosphorylated oligosaccharides per enzyme. While such bis-phosphorylated oligosaccharides may be naturally present on the enzyme, it should be noted that the enzymes may be modified to possess such oligosaccharides. For example, suitable replacement enzymes may be modified by certain enzymes which are capable of catalyzing the transfer of N-acetylglucosamine-L-phosphate from UDP-GlcNAc to the 6' position of α-1,2-linked mannoses on lysosomal enzymes. Methods and compositions for producing and using such enzymes are described by, for example, Canfield et al. in U.S. Pat. Nos. 6,537,785, 6,534,300, each incorporated herein by reference.

In some embodiments, replacement enzymes for use in the present invention may be conjugated or fused to a lysosomal targeting moiety that is capable of binding to a receptor on the surface of brain cells. A suitable lysosomal targeting moiety can be IGF-I, IGF-II, RAP, p97, and variants, homologues or fragments thereof (e.g., including those peptide having a sequence at least 70%, 75%, 80%, 85%, 90%, or 95% identical to a wild-type mature human IGF-I, IGF-II, RAP, p97 peptide sequence).

In some embodiments, replacement enzymes suitable for the present invention have not been modified to enhance delivery or transport of such agents across the BBB and into the CNS.

In some embodiments, a therapeutic protein includes a targeting moiety (e.g., a lysosome targeting sequence) and/or a membrane-penetrating peptide. In some embodiments, a targeting sequence and/or a membrane-penetrating peptide is an intrinsic part of the recombinant arylsulfatase A (e.g., via a chemical linkage, via a fusion protein). In some embodiments, a targeting sequence contains a mannose-6-phosphate moiety. In some embodiments, a targeting sequence contains an IGF-I moiety. In some embodiments, a targeting sequence contains an IGF-II moiety.

Formulations

Aqueous pharmaceutical solutions and compositions (i.e., formulations) that are traditionally used to deliver therapeutic agents to the CNS of a subject include unbuffered isotonic saline and Elliott's B solution, which is artificial CSF. A comparison depicting the compositions of CSF relative to Elliott's B solution is included in Table 2 below. As shown in Table 2, the concentration of Elliot's B Solution closely parallels that of the CSF. Elliott's B Solution, however contains a very low buffer concentration and accordingly may not provide the adequate buffering capacity needed to stabilize therapeutic agents (e.g., proteins), especially over extended periods of time (e.g., during storage conditions). Furthermore, Elliott's B Solution contains certain salts which may be incompatible with the formulations intended to deliver some therapeutic agents, and in particular proteins or enzymes. For example, the calcium salts present in Elliott's B Solution are capable of mediating protein precipitation and thereby reducing the stability of the formulation.

TABLE 2

| Solution | $Na^+$ mEq/L | $K^+$ mEq/L | $Ca^{++}$ mEq/L | $Mg^{++}$ mEq/L | $HCO3^-$ mEq/L | $Cl^-$ mEq/L | pH | Phosphorous mg/L | Glucose mg/L |
|---|---|---|---|---|---|---|---|---|---|
| CSF | 117-137 | 2.3 | 2.2 | 2.2 | 22.9 | 113-127 | 7.31 | 1.2-2.1 | 45-80 |
| Elliott's B Sol'n | 149 | 2.6 | 2.7 | 2.4 | 22.6 | 132 | 6.0-7.5 | 2.3 | 80 |

The present invention provides formulations, in either aqueous, pre-lyophilized, lyophilized or reconstituted form, for therapeutic agents that have been formulated such that they are capable of stabilizing, or alternatively slowing or preventing the degradation, of one or more therapeutic agents formulated therewith (e.g., recombinant proteins). In some embodiments, the present formulations provide lyophilization formulation for therapeutic agents. In some embodiments, the present formulations provide aqueous formulations for therapeutic agents. In some embodiments the formulations are stable formulations.

Stable Formulations

As used herein, the term "stable" refers to the ability of the therapeutic agent (e.g., a recombinant enzyme) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., preferably for at least 1, 3, 6, 12, 18, 24, 30, 36 months or more). In the context of a formulation a stable formulation is one in which the therapeutic agent therein essentially retains its physical and/or chemical integrity and biological activity upon storage and during processes (such as freeze/thaw, mechanical mixing and lyophilization). For protein stability, it can be measure by formation of high molecular weight (HMW) aggregates, loss of enzyme activity, generation of peptide fragments and shift of charge profiles.

Stability of the therapeutic agent is of particular importance with respect to the maintenance of the specified range of the therapeutic agent concentration required to enable the agent to serve its intended therapeutic function. Stability of the therapeutic agent may be further assessed relative to the biological activity or physiochemical integrity of the therapeutic agent over extended periods of time. For example, stability at a given time point may be compared against stability at an earlier time point (e.g., upon formulation day 0) or against unformulated therapeutic agent and the results of this comparison expressed as a percentage. Preferably, the pharmaceutical compositions of the present invention maintain at least 100%, at least 99%, at least 98%, at least 97% at least 95%, at least 90%, at least 85%, at least 80%, at least 75%, at least 70%, at least 65%, at least 60%, at least 55% or at least 50% of the therapeutic agent's biological activity or physiochemical integrity over an extended period of time (e.g., as measured over at least about 6-12 months, at room temperature or under accelerated storage conditions).

The therapeutic agents are preferably soluble in the pharmaceutical compositions of the present invention. The term "soluble" as it relates to the therapeutic agents of the present invention refer to the ability of such therapeutic agents to form a homogenous solution. Preferably the solubility of the therapeutic agent in the solution into which it is administered and by which it is transported to the target site of action (e.g., the cells and tissues of the brain) is sufficient to permit the delivery of a therapeutically effective amount of the therapeutic agent to the targeted site of action. Several factors can impact the solubility of the therapeutic agents. For example, relevant factors which may impact protein solubility include ionic strength, amino acid sequence and the presence of other co-solubilizing agents or salts (e.g., calcium salts.) In some embodiments, the pharmaceutical compositions are formulated such that calcium salts are excluded from such compositions.

Suitable formulations, in either aqueous, pre-lyophilized, lyophilized or reconstituted form, may contain a therapeutic agent of interest (e.g., recombinant human arylsulfatase A) at various concentrations. In some embodiments, formulations may contain a protein or therapeutic agent of interest at a concentration in the range of about 0.1 mg/ml to 100 mg/ml (e.g., about 0.1 mg/ml to 80 mg/ml, about 0.1 mg/ml to 60 mg/ml, about 0.1 mg/ml to 50 mg/ml, about 0.1 mg/ml to 40 mg/ml, about 0.1 mg/ml to 30 mg/ml, about 0.1 mg/ml to 25 mg/ml, about 0.1 mg/ml to 20 mg/ml, about 0.1 mg/ml to 60 mg/ml, about 0.1 mg/ml to 50 mg/ml, about 0.1 mg/ml to 40 mg/ml, about 0.1 mg/ml to 30 mg/ml, about 0.1 mg/ml to 25 mg/ml, about 0.1 mg/ml to 20 mg/ml, about 0.1 mg/ml to 15 mg/ml, about 0.1 mg/ml to 10 mg/ml, about 0.1 mg/ml to 5 mg/ml, about 1 mg/ml to 10 mg/ml, about 1 mg/ml to 20 mg/ml, about 1 mg/ml to 40 mg/ml, about 5 mg/ml to 100 mg/ml, about 5 mg/ml to 50 mg/ml, or about 5 mg/ml to 25 mg/ml). In some embodiments, formulations according to the invention may contain a therapeutic agent at a concentration of at least or at approximately 1 mg/ml, 5 mg/ml, 10 mg/ml, 15 mg/ml, 20 mg/ml, 25 mg/ml, 30 mg/ml, 40 mg/ml, 50 mg/ml, 60 mg/ml, 70 mg/ml, 80 mg/ml, 90 mg/ml, or 100 mg/ml. In some embodiments, formulations contain a therapeutic agent at a concentration of at least or at approximately 25 mg/ml. In some embodiments, formulations contain a therapeutic agent at a concentration of at least or at approximately 30 mg/ml.

The formulations of the present invention are characterized by their tolerability either as aqueous solutions or as reconstituted lyophilized solutions. As used herein, the terms "tolerable" and "tolerability" refer to the ability of the pharmaceutical compositions of the present invention to not elicit an adverse reaction in the subject to whom such composition is administered, or alternatively not to elicit a serious adverse reaction in the subject to whom such composition is administered. In some embodiments, the pharmaceutical compositions of the present invention are well tolerated by the subject to whom such compositions is administered.

Many therapeutic agents, and in particular the proteins and enzymes of the present invention, require controlled pH and specific excipients to maintain their solubility and stability in the pharmaceutical compositions of the present invention. Table 3 below identifies typical aspects of protein formulations considered to maintain the solubility and stability of the protein therapeutic agents of the present invention.

TABLE 3

| Parameter | Typical Range/Type | Rationale |
| --- | --- | --- |
| pH | 5 to 7.5 | For stability<br>Sometimes also for solubility |
| Buffer type | acetate, succinate, citrate, histidine, phosphate or Tris | To maintain optimal pH<br>May also affect stability |
| Buffer concentration | 5-50 mM | To maintain pH<br>May also stabilize or add ionic strength |
| Tonicifier | NaCl, sugars, mannitol | To render iso-osmotic or isotonic solutions |
| Surfactant | Polysorbate 20, polysorbate 80 | To stabilize against interfaces and shear |
| Other | Amino acids (e.g. arginine) at tens to hundreds of mM | For enhanced solubility or stability |

Buffers

The pH of the formulation is an additional factor which is capable of altering the solubility of a therapeutic agent (e.g., an enzyme or protein) in an aqueous formulation or for a pre-lyophilization formulation. Accordingly the formulations of the present invention preferably comprise one or more buffers. In some embodiments the aqueous formulations comprise an amount of buffer sufficient to maintain the optimal pH of said composition between about 4.0-8.0 (e.g., about 4.0, 4.5, 5.0, 5.5, 6.0, 6.2, 6.4, 6.5, 6.6, 6.8, 7.0, 7.5, or 8.0). In some embodiments, the pH of the formulation is between about 5.0-7.5, between about 5.5-7.0, between about 6.0-7.0, between about 5.5-6.0, between about 5.5-6.5, between about 5.0-6.0, between about 5.0-6.5 and between about 6.0-7.5. Suitable buffers include, for example acetate, citrate, histidine, phosphate, succinate, tris(hydroxymethyl) aminomethane ("Tris") and other organic acids. In some embodiments, the buffer is phosphate.

The buffer concentration and pH range of the pharmaceutical compositions of the present invention are factors in controlling or adjusting the tolerability of the formulation. In some embodiments, a buffering agent is present at a concentration ranging between about 1 mM to about 150 mM, or between about 10 mM to about 50 mM, or between about 15 mM to about 50 mM, or between about 20 mM to about 50 mM, or between about 25 mM to about 50 mM. In some embodiments, a suitable buffering agent is present at a concentration of approximately 1 mM, 5 mM, 10 mM, 15 mM, 20 mM, 25 mM, 30 mM, 35 mM, 40 mM, 45 mM 50 mM, 75 mM, 100 mM, 125 mM or 150 mM.

In some embodiments, the buffer is present at a concentration no greater than an upper limit, e.g., approximately 100 mM, 90 mM, 80 mM, 60 mM, 50 mM, 40 mM, 30 mM, 20 mM, 10 mM, or 5 mM. In some embodiments, the buffer is present at a concentration no greater than approximately 50 mM. In some embodiments, the buffer is present at a concentration no greater than approximately 25 mM. In some embodiments, the buffer is present at a concentration no greater than approximately 20 mM. In some embodiments, the buffer is present at a concentration no greater than approximately 10 mM. In some embodiments, the buffer is present at a concentration no greater than approximately 5 mM.

Tonicity

In some embodiments, formulations, in either aqueous, pre-lyophilized, lyophilized or reconstituted form, contain an isotonicity agent to keep the formulations isotonic. Typically, by "isotonic" is meant that the formulation of interest has essentially the same osmotic pressure as human blood. Isotonic formulations will generally have an osmotic pressure from about 240 mOsm/kg to about 350 mOsm/kg.

Isotonicity can be measured using, for example, a vapor pressure or freezing point type osmometers. Exemplary isotonicity agents include, but are not limited to, glycine, sorbitol, mannitol, sodium chloride and arginine. In some embodiments, suitable isotonic agents may be present in aqueous and/or pre-lyophilized formulations at a concentration from about 0.01-5% (e.g., 0.05, 0.1, 0.15, 0.2, 0.3, 0.4, 0.5, 0.75, 1.0, 1.25, 1.5, 2.0, 2.5, 3.0, 4.0 or 5.0%) by weight. In some embodiments, formulations for lyophilization contain an isotonicity agent to keep the pre-lyophilization formulations or the reconstituted formulations isotonic.

While generally isotonic solutions are preferred for parenterally administered drugs, the use of isotonic solutions may change solubility for some therapeutic agents and in particular some proteins and/or enzymes. Slightly hypertonic solutions (e.g., up to 175 mM sodium chloride in 5 mM sodium phosphate at pH 7.0) and sugar-containing solutions (e.g., up to 2% sucrose in 5 mM sodium phosphate at pH 7.0) have been demonstrated to be well tolerated. The most common approved CNS bolus formulation composition is saline (about 150 mM NaCl in water).

Stabilizing Agents

In some embodiments, formulations may contain a stabilizing agent, or lyoprotectant, to protect the protein. Typically, a suitable stabilizing agent is a sugar, a non-reducing sugar and/or an amino acid. Exemplary sugars include, but are not limited to, dextran, lactose, mannitol, mannose, sorbitol, raffinose, sucrose and trehalose. Exemplary amino acids include, but are not limited to, arginine, glycine and methionine. Additional stabilizing agents may include sodium chloride, hydroxyethyl starch and polyvinylpyrolidone. The amount of stabilizing agent in the lyophilized formulation is generally such that the formulation will be isotonic. However, hypertonic reconstituted formulations may also be suitable. In addition, the amount of stabilizing agent must not be too low such that an unacceptable amount of degradation/aggregation of the therapeutic agent occurs. Exemplary stabilizing agent concentrations in the formulation may range from about 1 mM to about 400 mM (e.g., from about 30 mM to about 300 mM, and from about 50 mM to about 100 mM), or alternatively, from 0.1% to 15% (e.g., from 1% to 10%, from 5% to 15%, from 5% to 10%) by weight. In some embodiments, the ratio of the mass amount of the stabilizing agent and the therapeutic agent is about 1:1. In other embodiments, the ratio of the mass amount of the stabilizing agent and the therapeutic agent can be about 0.1:1, 0.2:1, 0.25:1, 0.4:1, 0.5:1, 1:1, 2:1, 2.6:1, 3:1, 4:1, 5:1, 10:1, or 20:1. In some embodiments, suitable for lyophilization, the stabilizing agent is also a lyoprotectant.

In some embodiments, liquid formulations suitable for the present invention contain amorphous materials. In some embodiments, liquid formulations suitable for the present invention contain a substantial amount of amorphous materials (e.g., sucrose-based formulations). In some embodiments, liquid formulations suitable for the present invention contain partly crystalline/partly amorphous materials.

Bulking Agents

In some embodiments, suitable formulations for lyophilization may further include one or more bulking agents. A "bulking agent" is a compound which adds mass to the lyophilized mixture and contributes to the physical structure of the lyophilized cake. For example, a bulking agent may improve the appearance of lyophilized cake (e.g., essentially uniform lyophilized cake). Suitable bulking agents include, but are not limited to, sodium chloride, lactose, mannitol, glycine, sucrose, trehalose, hydroxyethyl starch. Exemplary concentrations of bulking agents are from about 1% to about 10% (e.g., 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, and 10.0%).

Surfactants

In some embodiments, it is desirable to add a surfactant to formulations. Exemplary surfactants include nonionic surfactants such as Polysorbates (e.g., Polysorbates 20 or 80); poloxamers (e.g., poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristarnidopropyl-, palmidopropyl-, or isostearamidopropyl-dimethylamine; sodium methyl cocoyl-, or disodium methyl ofeyl-taurate; and the MONAQUAT™ series (Mona Industries, Inc., Paterson, N.J.), polyethyl glycol, polypropyl glycol, and copolymers of ethylene and propylene glycol (e.g., Pluronics, PF68, etc.). Typically, the amount of surfactant added is such that it reduces aggregation of the protein and minimizes the formation of particulates or effervescences. For example, a surfactant may be present in a formulation at a concentration from about 0.001-0.5% (e.g., about 0.005-0.05%, or 0.005-0.01%). In particular, a surfactant may be present in a formulation at a concentration of approximately 0.005%, 0.01%, 0.02%, 0.1%, 0.2%, 0.3%, 0.4%, or 0.5%, etc. Alternatively, or in addition, the surfactant may be added to the lyophilized formulation, pre-lyophilized formulation and/or the reconstituted formulation.

Other pharmaceutically acceptable carriers, excipients or stabilizers such as those described in Remington's Pharmaceutical Sciences 16th edition, Osol, A. Ed. (1980) may be included in the formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include, but are not limited to, additional buffering agents; preservatives; co-solvents; antioxidants including ascorbic acid and methionine; chelating agents such as EDTA; metal complexes (e.g., Zn-protein complexes); biodegradable polymers such as polyesters; and/or salt-forming counterions such as sodium.

Formulations, in either aqueous, pre-lyophilized, lyophilized or reconstituted form, in accordance with the present invention can be assessed based on product quality analysis, reconstitution time (if lyophilized), quality of reconstitution (if lyophilized), high molecular weight, moisture, and glass transition temperature. Typically, protein quality and product analysis include product degradation rate analysis using methods including, but not limited to, size exclusion HPLC (SE-HPLC), cation exchange-HPLC (CEX-HPLC), X-ray diffraction (XRD), modulated differential scanning calorimetry (mDSC), reversed phase HPLC (RP-HPLC), multi-angle light scattering (MALS), fluorescence, ultraviolet absorption, nephelometry, capillary electrophoresis (CE), SDS-PAGE, and combinations thereof. In some embodiments, evaluation of product in accordance with the present invention may include a step of evaluating appearance (either liquid or cake appearance).

Generally, formulations (lyophilized or aqueous) can be stored for extended periods of time at room temperature. Storage temperature may typically range from 0° C. to 45° C. (e.g., 4° C., 20° C., 25° C., 45° C. etc.). Formulations may be stored for a period of months to a period of years. Storage time generally will be 24 months, 12 months, 6 months, 4.5 months, 3 months, 2 months or 1 month. Formulations can be stored directly in the container used for administration, eliminating transfer steps.

Formulations can be stored directly in the lyophilization container (if lyophilized), which may also function as the reconstitution vessel, eliminating transfer steps. Alternatively, lyophilized product formulations may be measured into smaller increments for storage. Storage should generally avoid circumstances that lead to degradation of the proteins, including but not limited to exposure to sunlight, UV radiation, other forms of electromagnetic radiation, excessive heat or cold, rapid thermal shock, and mechanical shock.

Lyophilization

Inventive methods in accordance with the present invention can be utilized to lyophilize any materials, in particular, therapeutic agents. Typically, a pre-lyophilization formulation further contains an appropriate choice of excipients or other components such as stabilizers, buffering agents, bulking agents, and surfactants to prevent compound of interest from degradation (e.g., protein aggregation, deamidation, and/or oxidation) during freeze-drying and storage. The formulation for lyophilization can include one or more additional ingredients including lyoprotectants or stabilizing agents, buffers, bulking agents, isotonicity agents and surfactants.

After the substance of interest and any additional components are mixed together, the formulation is lyophilized Lyophilization generally includes three main stages: freezing, primary drying and secondary drying. Freezing is necessary to convert water to ice or some amorphous formulation components to the crystalline form. Primary drying is the process step when ice is removed from the frozen product by direct sublimation at low pressure and temperature. Secondary drying is the process step when bounded water is removed from the product matrix utilizing the diffusion of residual water to the evaporation surface. Product temperature during secondary drying is normally higher than during primary drying. See, Tang X. et al. (2004) "Design of freeze-drying processes for pharmaceuticals: Practical advice," *Pharm. Res.*, 21:191-200; Nail S. L. et al. (2002) "Fundamentals of freeze-drying," in Development and manufacture of protein pharmaceuticals. Nail S. L. editor New York: Kluwer Academic/Plenum Publishers, pp 281-353; Wang et al. (2000) "Lyophilization and development of solid protein pharmaceuticals," *Int. J. Pharm.*, 203:1-60; Williams N. A. et al. (1984) "The lyophilization of pharmaceuticals; A literature review." *J. Parenteral Sci. Technol.*, 38:48-59. Generally, any lyophilization process can be used in connection with the present invention.

In some embodiments, an annealing step may be introduced during the initial freezing of the product. The annealing step may reduce the overall cycle time. Without wishing to be bound by any theories, it is contemplated that the annealing step can help promote excipient crystallization and formation of larger ice crystals due to re-crystallization of small crystals formed during supercooling, which, in turn, improves reconstitution. Typically, an annealing step includes an interval or oscillation in the temperature during freezing. For example, the freeze temperature may be $-40°$ C., and the annealing step will increase the temperature to, for example, $-10°$ C. and maintain this temperature for a set period of time. The annealing step time may range from 0.5 hours to 8 hours (e.g., 0.5, 1.0 1.5, 2.0, 2.5, 3, 4, 6, and 8 hours). The annealing temperature may be between the freezing temperature and $0°$ C.

Lyophilization may be performed in a container, such as a tube, a bag, a bottle, a tray, a vial (e.g., a glass vial), syringe or any other suitable containers. The containers may be disposable. Lyophilization may also be performed in a large scale or small scale. In some instances, it may be desirable to lyophilize the protein formulation in the container in which reconstitution of the protein is to be carried out in order to avoid a transfer step. The container in this instance may, for example, be a 3, 4, 5, 10, 20, 50 or 100 cc vial.

Many different freeze-dryers are available for this purpose such as Hull pilot scale dryer (SP Industries, USA), Genesis (SP Industries) laboratory freeze-dryers, or any freeze-dryers capable of controlling the given lyophilization process parameters. Freeze-drying is accomplished by freezing the formulation and subsequently subliming ice from the frozen content at a temperature suitable for primary drying. Initial freezing brings the formulation to a temperature below about $-20°$ C. (e.g., $-50°$ C., $-45°$ C., $-40°$ C., $-35°$ C., $-30°$ C., $-25°$ C., etc.) in typically not more than about 4 hours (e.g., not more than about 3 hours, not more than about 2.5 hours, not more than about 2 hours). Under this condition, the product temperature is typically below the eutectic point or the collapse temperature of the formulation. Typically, the shelf temperature for the primary drying will range from about $-30$ to $25°$ C. (provided the product remains below the melting point during primary drying) at a suitable pressure, ranging typically from about 20 to 250 mTorr. The formulation, size and type of the container holding the sample (e.g., glass vial) and the volume of liquid will mainly dictate the time required for drying, which can range from a few hours to several days. A secondary drying stage is carried out at about 0-60° C., depending primarily on the type and size of container and the type of therapeutic protein employed. Again, volume of liquid will mainly dictate the time required for drying, which can range from a few hours to several days.

As a general proposition, lyophilization will result in a lyophilized formulation in which the moisture content thereof is less than about 5%, less than about 4%, less than about 3%, less than about 2%, less than about 1%, and less than about 0.5%.

Reconstitution

While the pharmaceutical compositions of the present invention are generally in an aqueous form upon administration to a subject, in some embodiments the pharmaceutical compositions of the present invention are lyophilized Such compositions must be reconstituted by adding one or more diluents thereto prior to administration to a subject. At the desired stage, typically at an appropriate time prior to administration to the patient, the lyophilized formulation may be reconstituted with a diluent such that the protein concentration in the reconstituted formulation is desirable.

Various diluents may be used in accordance with the present invention. In some embodiments, a suitable diluent for reconstitution is water. The water used as the diluent can be treated in a variety of ways including reverse osmosis, distillation, deionization, filtrations (e.g., activated carbon, microfiltration, nanofiltration) and combinations of these treatment methods. In general, the water should be suitable for injection including, but not limited to, sterile water or bacteriostatic water for injection.

Additional exemplary diluents include a pH buffered solution (e.g., phosphate-buffered saline), sterile saline solution, Elliot's solution, Ringer's solution or dextrose solution. Suitable diluents may optionally contain a preservative. Exemplary preservatives include aromatic alcohols such as benzyl or phenol alcohol. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0%, from about 0.5-1.5%, or about 1.0-1.2%.

Diluents suitable for the invention may include a variety of additives, including, but not limited to, pH buffering agents, (e.g. Tris, histidine,) salts (e.g., sodium chloride) and other additives (e.g., sucrose) including those described above (e.g. stabilizing agents, isotonicity agents).

According to the present invention, a lyophilized substance (e.g., protein, such as recombinant human arylsulftase A) can be reconstituted to a concentration of at least 25 mg/ml (e.g., at least 50 mg/ml, at least 75 mg/ml, at least 100 mg/) and in any ranges therebetween. In some embodiments, a lyophilized substance (e.g., protein) may be reconstituted to a concentration ranging from about 1 mg/ml to 100 mg/ml (e.g., from about 1 mg/ml to 50 mg/ml, from 1 mg/ml to 100 mg/ml, from about 1 mg/ml to about 5 mg/ml, from about 1 mg/ml to about 10 mg/ml, from about 1 mg/ml to about 25 mg/ml, from about 1 mg/ml to about 75 mg/ml, from about 10 mg/ml to about 30 mg/ml, from about 10 mg/ml to about 50 mg/ml, from about 10 mg/ml to about 75 mg/ml, from about 10 mg/ml to about 100 mg/ml, from about 25 mg/ml to about 50 mg/ml, from about 25 mg/ml to about 75 mg/ml, from about 25 mg/ml to about 100 mg/ml, from about 50 mg/ml to about 75 mg/ml, from about 50 mg/ml to about 100 mg/ml). In some embodiments, the concentration of protein in the reconstituted formulation may be higher than the concentration in the pre-lyophilization formulation. In some embodiments, the lyophilized substance is reconstituted to a concentration of at least 25 mg/mL, for example, 30 mg/mL. High protein concentrations in the reconstituted formulation are considered to be particularly useful where subcutaneous or intramuscular delivery of the reconstituted formulation is intended. In some embodiments, the protein concentration in the reconstituted formulation may be about 2-50 times (e.g., about 2-20, about 2-10 times, or about 2-5 times) of the pre-lyophilized formulation. In some embodiments, the protein concentration in the reconstituted formulation may be at least about 2 times (e.g., at least about 3, 4, 5, 10, 20, 40 times) of the pre-lyophilized formulation.

Reconstitution according to the present invention may be performed in any container. Exemplary containers suitable for the invention include, but are not limited to, such as tubes, vials, syringes (e.g., single-chamber or dual-chamber), bags, bottles, and trays. Suitable containers may be made of any materials such as glass, plastics, metal. The containers may be disposable or reusable. Reconstitution may also be performed in a large scale or small scale.

In some instances, it may be desirable to lyophilize the protein formulation in the container in which reconstitution of the protein is to be carried out in order to avoid a transfer step. The container in this instance may, for example, be a 3, 4, 5, 10, 20, 50 or 100 cc vial. In some embodiments, a suitable container for lyophilization and reconstitution is a dual chamber syringe (e.g., Lyo-Ject® (Vetter) syringes). For example, a dual chamber syringe may contain both the lyophilized substance and the diluent, each in a separate chamber, separated by a stopper (see Example 5). To reconstitute, a plunger can be attached to the stopper at the diluent side and pressed to move diluent into the product chamber so that the diluent can contact the lyophilized substance and reconstitution may take place as described herein (see Example 5).

The pharmaceutical compositions, formulations and related methods of the invention are useful for delivering a variety of therapeutic agents to the CNS of a subject (e.g., intrathecally, intraventricularly or intracisternally) and for the treatment of the associated diseases. The pharmaceutical compositions of the present invention are particularly useful for delivering proteins and enzymes (e.g., enzyme replacement therapy) to subjects suffering from lysosomal storage disorders. The lysosomal storage diseases represent a group of relatively rare inherited metabolic disorders that result from defects in lysosomal function. The lysosomal diseases are characterized by the accumulation of undigested macromolecules within the lysosomes, which results in an increase in the size and number of such lysosomes and ultimately in cellular dysfunction and clinical abnormalities.

CNS Delivery

It is contemplated that various stable formulations described herein are generally suitable for CNS delivery of therapeutic agents. Stable formulations according to the present invention can be used for CNS delivery via various techniques and routes including, but not limited to, intra-parenchymal, intracerebral, intravetricular cerebral (ICV), intrathecal (e.g., IT-Lumbar, IT-cisterna magna) administrations and any other techniques and routes for injection directly or indirectly to the CNS and/or CSF. The term "cisterna magna" refers to the space around and below the cerebellum via the opening between the skull and the top of the spine. Typically, injection via cisterna magna is also referred to as "cisterna magna delivery."

Intrathecal Delivery

In some embodiments, a replacement enzyme is delivered to the CNS in a formulation described herein. In some embodiments, a replacement enzyme is delivered to the CNS by administering into the cerebrospinal fluid (CSF) of a subject in need of treatment. In some embodiments, intrathecal administration is used to deliver a desired replacement enzyme (e.g., an ASA protein) into the CSF. As used herein, intrathecal administration (also referred to as intrathecal injection) refers to an injection into the spinal canal (intrathecal space surrounding the spinal cord). Various techniques may be used including, without limitation, lumbar puncture. Exemplary methods are described in Lazorthes et al. Advances in Drug Delivery Systems and Applications in Neurosurgery, 143-192, the contents of which are incorporated herein by reference.

According to the present invention, an enzyme may be injected at any region surrounding the spinal canal. In some embodiments, an enzyme is injected into the lumbar area. As used herein, the term "lumbar region" or "lumbar area" refers to the area between the third and fourth lumbar (lower back) vertebrae and, more inclusively, the L2-S1 region of the spine. Typically, intrathecal injection via the lumbar region or lumber area is also referred to as "lumbar intrathecal delivery" or "lumbar intrathecal administration."

In some embodiments, therapeutic proteins, e.g., recombinant arylsulfatase A is delivered by lumbar intrathecal administration, for example, delivered between the third and fourth lumbar (lower back) vertebrae and, more inclusively, the L2-S1 region of the spine. It is contemplated that lumbar intrathecal administration or delivery distinguishes over cisterna magna delivery in that lumbar intrathecal administration or delivery according to the present invention provides better and more effective delivery to the distal spinal canal, while cisterna magna delivery, among other things, typically does not deliver well to the distal spinal canal.

Device for Intrathecal Delivery

Various devices may be used for intrathecal delivery according to the present invention. In some embodiments, a device for intrathecal administration contains a fluid access port (e.g., injectable port); a hollow body (e.g., catheter) having a first flow orifice in fluid communication with the fluid access port and a second flow orifice configured for insertion into spinal cord; and a securing mechanism for securing the insertion of the hollow body in the spinal cord. As a non-limiting example, a suitable securing mechanism contains one or more nobs mounted on the surface of a hollow body and a sutured ring adjustable over the one or more nobs to prevent the hollow body (e.g., catheter) from slipping out of the spinal cord. In various embodiments, the fluid access port comprises a reservoir. In some embodiments, the fluid access port comprises a mechanical pump (e.g., an infusion pump). In some embodiments, an implanted catheter is connected to either a reservoir (e.g., for bolus delivery), or an infusion pump. The fluid access port may be implanted or external.

In some embodiments, intrathecal administration may be performed by either lumbar puncture (i.e., slow bolus) or via a port-catheter delivery system (i.e., infusion or bolus). In some embodiments, the catheter is inserted between the laminae of the lumbar vertebrae and the tip is threaded up the thecal space to the desired level (generally L3-L4).

In some embodiments, intrathecal administration is through intermittent or continuous access to an implanted intrathecal drug delivery device (IDDD).

Relative to intravenous administration, a single dose volume suitable for intrathecal administration is typically small. Typically, intrathecal delivery according to the present invention maintains the balance of the composition of the CSF as well as the intracranial pressure of the subject. In some embodiments, intrathecal delivery is performed absent the corresponding removal of CSF from a subject. In some embodiments, a suitable single dose volume may be e.g., less than about 10 ml, 8 ml, 6 ml, 5 ml, 4 ml, 3 ml, 2 ml, 1.5 ml, 1 ml, or 0.5 ml. In some embodiments, a suitable single dose volume may be about 0.5-5 ml, 0.5-4 ml, 0.5-3 ml, 0.5-2 ml, 0.5-1 ml, 1-3 ml, 1-5 ml, 1.5-3 ml, 1-4 ml, or 0.5-1.5 ml. In some embodiments, intrathecal delivery according to the present invention involves a step of removing a desired amount of CSF first. In some embodiments, less than about 10 ml (e.g., less than about 9 ml, 8 ml, 7 ml, 6 ml, 5 ml, 4 ml, 3 ml, 2 ml, 1 ml) of CSF is first removed before intrathecal administration. In those cases, a suitable single dose volume may be e.g., more than about 3 ml, 4 ml, 5 ml, 6 ml, 7 ml, 8 ml, 9 ml, 10 ml, 15 ml, or 20 ml.

Other devices for intrathecal administration of therapeutic compositions or formulations to an individual are described in U.S. Pat. No. 6,217,552, incorporated herein by reference. Alternatively, the drug may be intrathecally given, for example, by a single injection, or continuous infusion. It should be understood that the dosage treatment may be in the form of a single dose administration or multiple doses.

For injection, formulations of the invention can be formulated in liquid solutions. In addition, the enzyme may be formulated in solid form and re-dissolved or suspended immediately prior to use. Lyophilized forms are also included. The injection can be, for example, in the form of a bolus injection or continuous infusion (e.g., using infusion pumps) of the enzyme.

Non-Intrathecal Delivery Methods

Therapeutic enzymes, e.g., recombinant arylsulfatase A, can be administered by non-intrathecal means, for example, by lateral cerebro ventricular injection into the brain of a subject. The injection can be made, for example, through a burr hole made in the subject's skull. In another embodiment, the enzyme and/or other pharmaceutical formulation is administered through a surgically inserted shunt into the cerebral ventricle of a subject. For example, the injection can be made into the lateral ventricles, which are larger. In some embodiments, injection into the third and fourth smaller ventricles can also be made.

Alternatively, pharmaceutical compositions can be administered by injection into the cisterna magna, or lumbar area of a subject.

Certain devices may be used to effect administration of a therapeutic composition. For example, formulations containing desired enzymes may be given using an Ommaya reservoir which is in common use for intrathecally administering drugs for meningeal carcinomatosis (Lancet 2: 983-84, 1963). More specifically, in this method, a ventricular tube is inserted through a hole formed in the anterior horn and is connected to an Ommaya reservoir installed under the scalp, and the reservoir is subcutaneously punctured to intrathecally deliver the particular enzyme being replaced, which is injected into the reservoir.

Slow Release/Sustained Delivery

In another embodiment of the method of the invention, the pharmaceutically acceptable formulation provides sustained delivery, e.g., "slow release" of the enzyme or other pharmaceutical composition used in the present invention, to a subject for at least one, two, three, four weeks or longer periods of time after the pharmaceutically acceptable formulation is administered to the subject.

As used herein, the term "sustained delivery" refers to continual delivery of a pharmaceutical formulation of the invention in vivo over a period of time following administration, preferably at least several days, a week or several weeks. Sustained delivery of the composition can be demonstrated by, for example, the continued therapeutic effect of the enzyme over time (e.g., sustained delivery of the enzyme can be demonstrated by continued reduced amount of storage granules in the subject). Alternatively, sustained delivery of the enzyme may be demonstrated by detecting the presence of the enzyme in vivo over time.

Delivery to Target Tissues

As discussed above, one of the surprising and important features of the present invention is that therapeutic agents, in particular, replacement enzymes administered using inventive methods and compositions of the present invention are able to effectively and extensively diffuse across the brain surface and penetrate various layers or regions of the brain, including deep brain regions. In addition, inventive methods and compositions of the present invention effectively deliver therapeutic agents (e.g., an ASA enzyme) to various tissues, neurons or cells of spinal cord, including the lumbar region, which is hard to target by existing CNS delivery methods such as ICV injection. Furthermore, inventive methods and compositions of the present invention deliver sufficient amount of therapeutic agents (e.g., an ASA enzyme) to blood stream and various peripheral organs and tissues.

Thus, in some embodiments, a therapeutic protein (e.g., an ASA enzyme) is delivered to the central nervous system of a subject. In some embodiments, a therapeutic protein (e.g., an ASA enzyme) is delivered to one or more of target tissues of brain, spinal cord, and/or peripheral organs. As used herein, the term "target tissues" refers to any tissue that is affected by the lysosomal storage disease to be treated or any tissue in which the deficient lysosomal enzyme is normally expressed. In some embodiments, target tissues include those tissues in which there is a detectable or abnormally high amount of enzyme substrate, for example stored in the cellular lysosomes of the tissue, in patients suffering from or susceptible to the lysosomal storage disease. In some embodiments, target tissues include those tissues that display disease-associated pathology, symptom, or feature. In some embodiments, target tissues include those tissues in which the deficient lysosomal enzyme is normally expressed at an elevated level. As used herein, a target tissue may be a brain target tissue, a spinal cord target tissue and/or a peripheral target tissue. Exemplary target tissues are described in detail below.

Brain Target Tissues

In general, the brain can be divided into different regions, layers and tissues. For example, meningeal tissue is a system of membranes which envelops the central nervous system, including the brain. The meninges contain three layers, including dura matter, arachnoid matter, and pia matter. In general, the primary function of the meninges and of the cerebrospinal fluid is to protect the central nervous system. In some embodiments, a therapeutic protein in accordance with the present invention is delivered to one or more layers of the meninges.

The brain has three primary subdivisions, including the cerebrum, cerebellum, and brain stem. The cerebral hemispheres, which are situated above most other brain structures and are covered with a cortical layer. Underneath the cerebrum lies the brainstem, which resembles a stalk on which the cerebrum is attached. At the rear of the brain, beneath the cerebrum and behind the brainstem, is the cerebellum.

The diencephalon, which is located near the midline of the brain and above the mesencephalon, contains the thalamus, metathalamus, hypothalamus, epithalamus, prethalamus, and pretectum. The mesencephalon, also called the midbrain, contains the tectum, tegumentum, ventricular mesocoelia, and cerebral peduncels, the red nucleus, and the cranial nerve III nucleus. The mesencephalon is associated with vision, hearing, motor control, sleep/wake, alertness, and temperature regulation.

Regions of tissues of the central nervous system, including the brain, can be characterized based on the depth of the tissues. For example, CNS (e.g., brain) tissues can be characterized as surface or shallow tissues, mid-depth tissues, and/or deep tissues.

According to the present invention, a therapeutic protein (e.g., a replacement enzyme) may be delivered to any appropriate brain target tissue(s) associated with a particular disease to be treated in a subject. In some embodiments, a therapeutic protein (e.g., a replacement enzyme) in accordance with the present invention is delivered to surface or shallow brain target tissue. In some embodiments, a therapeutic protein in accordance with the present invention is delivered to mid-depth brain target tissue. In some embodiments, a therapeutic protein in accordance with the present invention is delivered to deep brain target tissue. In some embodiments, a therapeutic protein in accordance with the present invention is delivered to a combination of surface or shallow brain target tissue, mid-depth brain target tissue, and/or deep brain target tissue. In some embodiments, a therapeutic protein in accordance with the present invention is delivered to a deep brain tissue at least 4 mm, 5 mm, 6 mm, 7 mm, 8 mm, 9 mm, 10 mm or more below (or internal to) the external surface of the brain.

In some embodiments, therapeutic agents (e.g., enzymes) are delivered to one or more surface or shallow tissues of cerebrum. In some embodiments, the targeted surface or shallow tissues of the cerebrum are located within 4 mm from the surface of the cerebrum. In some embodiments, the targeted surface or shallow tissues of the cerebrum are selected from pia mater tissues, cerebral cortical ribbon tissues, hippocampus, Virchow Robin space, blood vessels within the VR space, the hippocampus, portions of the hypothalamus on the inferior surface of the brain, the optic nerves and tracts, the olfactory bulb and projections, and combinations thereof.

In some embodiments, therapeutic agents (e.g., enzymes) are delivered to one or more deep tissues of the cerebrum. In some embodiments, the targeted surface or shallow tissues of the cerebrum are located 4 mm (e.g., 5 mm, 6 mm, 7 mm, 8 mm, 9 mm, or 10 mm) below (or internal to) the surface of the cerebrum. In some embodiments, targeted deep tissues of the cerebrum include the cerebral cortical ribbon. In some embodiments, targeted deep tissues of the cerebrum include one or more of the diencephalon (e.g., the hypothalamus, thalamus, prethalamus, subthalamus, etc.), metencephalon, lentiform nuclei, the basal ganglia, caudate, putamen, amygdala, globus pallidus, and combinations thereof.

In some embodiments, therapeutic agents (e.g., enzymes) are delivered to one or more tissues of the cerebellum. In certain embodiments, the targeted one or more tissues of the cerebellum are selected from the group consisting of tissues of the molecular layer, tissues of the Purkinje cell layer, tissues of the Granular cell layer, cerebellar peduncles, and combination thereof. In some embodiments, therapeutic agents (e.g., enzymes) are delivered to one or more deep tissues of the cerebellum including, but not limited to, tissues of the Purkinje cell layer, tissues of the Granular cell layer, deep cerebellar white matter tissue (e.g., deep relative to the Granular cell layer), and deep cerebellar nuclei tissue.

In some embodiments, therapeutic agents (e.g., enzymes) are delivered to one or more tissues of the brainstem. In some embodiments, the targeted one or more tissues of the brainstem include brain stem white matter tissue and/or brain stem nuclei tissue.

In some embodiments, therapeutic agents (e.g., enzymes) are delivered to various brain tissues including, but not limited to, gray matter, white matter, periventricular areas, pia-arachnoid, meninges, neocortex, cerebellum, deep tissues in cerebral cortex, molecular layer, caudate/putamen region, midbrain, deep regions of the pons or medulla, and combinations thereof.

In some embodiments, therapeutic agents (e.g., enzymes) are delivered to various cells in the brain including, but not limited to, neurons, glial cells, perivascular cells and/or meningeal cells. In some embodiments, a therapeutic protein is delivered to oligodendrocytes of deep white matter.

Spinal Cord

In general, regions or tissues of the spinal cord can be characterized based on the depth of the tissues. For example, spinal cord tissues can be characterized as surface or shallow tissues, mid-depth tissues, and/or deep tissues.

In some embodiments, therapeutic agents (e.g., enzymes) are delivered to one or more surface or shallow tissues of the spinal cord. In some embodiments, a targeted surface or shallow tissue of the spinal cord is located within 4 mm from the surface of the spinal cord. In some embodiments, a targeted surface or shallow tissue of the spinal cord contains pia matter and/or the tracts of white matter.

In some embodiments, therapeutic agents (e.g., enzymes) are delivered to one or more deep tissues of the spinal cord. In some embodiments, a targeted deep tissue of the spinal cord is located internal to 4 mm from the surface of the spinal cord. In some embodiments, a targeted deep tissue of the spinal cord contains spinal cord grey matter and/or ependymal cells.

In some embodiments, therapeutic agents (e.g., enzymes) are delivered to neurons of the spinal cord.

Peripheral Target Tissues

As used herein, peripheral organs or tissues refer to any organs or tissues that are not part of the central nervous system (CNS). Peripheral target tissues may include, but are not limited to, blood system, liver, kidney, heart, endothelium, bone marrow and bone marrow derived cells, spleen, lung, lymph node, bone, cartilage, ovary and testis. In some embodiments, a therapeutic protein (e.g., a replacement enzyme) in accordance with the present invention is delivered to one or more of the peripheral target tissues.

Biodistribution and Bioavailability

In various embodiments, once delivered to the target tissue, a therapeutic agent (e.g., an ASA enzyme) is localized intracellularly. For example, a therapeutic agent (e.g., enzyme) may be localized to exons, axons, lysosomes, mitochondria or vacuoles of a target cell (e.g., neurons such as Purkinje cells). For example, in some embodiments intrathecally-administered enzymes demonstrate translocation dynamics such that the enzyme moves within the perivascular space (e.g., by pulsation-assisted convective mechanisms). In addition, active axonal transport mechanisms relating to the association of the administered protein or enzyme with neurofilaments may also contribute to or otherwise facilitate the distribution of intrathecally-administered proteins or enzymes into the deeper tissues of the central nervous system.

In some embodiments, a therapeutic agent (e.g., an ASA enzyme) delivered according to the present invention may achieve therapeutically or clinically effective levels or activities in various targets tissues described herein. As used herein, a therapeutically or clinically effective level or activity is a level or activity sufficient to confer a therapeutic effect in a target tissue. The therapeutic effect may be objective (i.e., measurable by some test or marker) or subjective (i.e., subject gives an indication of or feels an effect). For example, a therapeutically or clinically effective level or activity may be an enzymatic level or activity that is sufficient to ameliorate symptoms associated with the disease in the target tissue (e.g., GAG storage).

In some embodiments, a therapeutic agent (e.g., a replacement enzyme) delivered according to the present invention may achieve an enzymatic level or activity that is at least 5%, 10%, 20%, 30%, 40%, 50%, 60%, 70%, 80%, 90%, 95% of the normal level or activity of the corresponding lysosomal enzyme in the target tissue. In some embodiments, a therapeutic agent (e.g., a replacement enzyme) delivered according to the present invention may achieve an enzymatic level or activity that is increased by at least 1-fold, 2-fold, 3-fold, 4-fold, 5-fold, 6-fold, 7-fold, 8-fold, 9-fold or 10-fold as compared to a control or to baseline (e.g., endogenous levels or activities without the treatment). In some embodiments, a therapeutic agent (e.g., a replacement enzyme) delivered according to the present invention may achieve an increased enzymatic level or activity at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg or 600 nmol/hr/mg in a target tissue.

In some embodiments, inventive methods according to the present invention are particularly useful for targeting the lumbar region. In some embodiments, a therapeutic agent (e.g., a replacement enzyme) delivered according to the present invention may achieve an increased enzymatic level or activity in the lumbar region of at least approximately 500 nmol/hr/mg, 600 nmol/hr/mg, 700 nmol/hr/mg, 800 nmol/hr/mg, 900 nmol/hr/mg, 1000 nmol/hr/mg, 1500 nmol/hr/mg, 2000 nmol/hr/mg, 3000 nmol/hr/mg, 4000 nmol/hr/mg, 5000 nmol/hr/mg, 6000 nmol/hr/mg, 7000 nmol/hr/mg, 8000 nmol/hr/mg, 9000 nmol/hr/mg, or 10,000 nmol/hr/mg.

In general, therapeutic agents (e.g., replacement enzymes) delivered according to the present invention have sufficiently long half time in CSF and target tissues of the brain, spinal cord, and peripheral organs. In some embodiments, a therapeutic agent (e.g., a replacement enzyme) delivered according to the present invention may have a half-life of at least approximately 30 minutes, 45 minutes, 60 minutes, 90 minutes, 2 hours, 3 hours, 4 hours, 5 hours, 6 hours, 7 hours, 8 hours, 9 hours, 10 hours, 12 hours, 16 hours, 18 hours, 20 hours, 25 hours, 30 hours, 35 hours, 40 hours, up to 3 days, up to 7 days, up to 14 days, up to 21 days or up to a month. In some embodiments, In some embodiments, a therapeutic agent (e.g., a replacement enzyme) delivered according to the present invention may retain detectable level or activity in CSF or bloodstream after 12 hours, 24 hours, 30 hours, 36 hours, 42 hours, 48 hours, 54 hours, 60 hours, 66 hours, 72 hours, 78 hours, 84 hours, 90 hours, 96 hours, 102 hours, or a week following administration. Detectable level or activity may be determined using various methods known in the art.

In certain embodiments, a therapeutic agent (e.g., a replacement enzyme) delivered according to the present invention achieves a concentration of at least 30 μg/ml in the CNS tissues and cells of the subject following administration (e.g., one week, 3 days, 48 hours, 36 hours, 24 hours, 18 hours, 12 hours, 8 hours, 6 hours, 4 hours, 3 hours, 2 hours, 1 hour, 30 minutes, or less, following intrathecal administration of the pharmaceutical composition to the subject). In certain embodiments, a therapeutic agent (e.g., a replacement enzyme) delivered according to the present invention achieves a concentration of at least 20 μg/ml, at least 15 μg/ml, at least 10 μg/ml, at least 7.5 μg/ml, at least 5 μg/ml, at least 2.5 μg/ml, at least 1.0 μg/ml or at least 0.5 μg/ml in the targeted tissues or cells of the subject (e.g., brain tissues or neurons) following administration to such subject (e.g., one week, 3 days, 48 hours, 36 hours, 24 hours, 18 hours, 12 hours, 8 hours, 6 hours, 4 hours, 3 hours, 2 hours, 1 hour, 30 minutes, or less following intrathecal administration of such pharmaceutical compositions to the subject).

Treatment of Metachromatic Leukodystrophy Disease (MLD)

Metachromatic Leukodystrophy Disease (MLD), also known as MLD Syndrome, is an autosomal recessive disorder resulting from a deficiency of the enzyme Arylsulfatease A (ASA). ASA, which is encoded by the ARSA gene in humans, is an enzyme that breaks down cerebroside 3-sulfate or sphingolipid 3-O-sulfogalactosylceramide (sulfatide) into cerebroside and sulfate. In the absence of the enzyme, sulfatides accumulate in the nervous system (e.g., myelin sheaths, neurons and glial cells) and to a lesser extent in visceral organs. The consequence of these molecular and cellular events is progressive demyelination and axonal loss within the CNS and PNS, which is accompanied clinically by severe motor and cognitive dysfunction.

A defining clinical feature of this disorder is central nervous system (CNS) degeneration, which results in cognitive impairment (e.g., mental retardation, nervous disorders, and blindness, among others).

MLD can manifest itself in young children (late-infantile form), where affected children typically begin showing symptoms just after the first year of life (e.g., at about 15-24 months), and generally do not survive past the age of 5 years. MLD can manifest itself in children (juvenile form), where affected children typically show cognitive impairment by about the age of 3-10 years, and life-span can vary (e.g., in the range of 10-15 years after onset of symptoms). MLD can manifest itself in adults (adult-onset form) and can appear in individuals of any age (e.g., typically at age 16 and later). The progression of the disease can vary greatly.

Compositions and methods of the present invention may be used to effectively treat individuals suffering from or susceptible to MLD. Certain methods of the invention for treating MLD generally comprise a step of administering intrathecally to a subject in need of treatment a recombinant arylsulfatase A (ASA) enzyme at a therapeutically effective dose and an administration interval for a treatment period sufficient to observe at least one indicator of treatment efficacy in the subject. According to many methods provided in the present disclosure, no serious adverse effects associated with administration of the recombinant arylsulfatase A are observed in the subject.

The terms, "treat" or "treatment," as used herein, refers to amelioration of one or more symptoms associated with the disease, prevention or delay of the onset of one or more symptoms of the disease, lessening of the severity or frequency of one or more symptoms of the disease, and/or slowing, stabilizing, or reducing the progression of disease-associated decline in one or more functions. Exemplary symptoms include, but are not limited to, intracranial pressure, hydrocephalus ex vacuo, accumulated sulfated glycolipids in the myelin sheaths in the central and peripheral nervous system and in visceral organs, progressive demyelination and axonal loss within the CNS and PNS, and/or motor and cognitive dysfunction.

In some embodiments, treatment refers to partially or complete alleviation, amelioration, relief, inhibition, delaying onset, reducing severity and/or incidence, slowing progression, stabilizating, or reversal of neurological impairment in an MLD patient. As used herein, the term "neurological impairment" includes various symptoms associated with impairment of the central nervous system (e.g., the brain and spinal cord). In some embodiments, various symptoms of MLD are associated with impairment of the peripheral nervous system (PNS).

Motor Functions

In some embodiments, neurological impairment in an MLD patient is characterized by decline in motor function, e.g., gross motor function. In some embodiments, treatment efficacy comprises a measure that relates to one or more motor functions.

In some embodiments, provided are methods of treating metachromatic leukodystrophy (MLD) Syndrome comprising a step of administering intrathecally to a subject in need of treatment a recombinant arylsulfatase A (ASA) enzyme at a therapeutically effective dose and an administration interval for a treatment period sufficient to improve, stabilize or reduce decline of one or more motor functions relative to baseline. In some embodiments, administering of the recombinant ASA enzyme further results in improvement, stabilization or reduction decline of one or more cognitive, adaptive, and/or executive functions.

The one or more motor functions may comprise, for example, gross motor function. It will be appreciated that gross motor function may be assessed by any appropriate method. For example, in some embodiments, gross motor function is measured as a change from a baseline in motor function using a Gross Motor Function Measure, such as the Gross Motor Function Measure-88 (GMFM-88) or Gross Motor Function Measure-66 (GMFM-66) total raw score or percentage. In some embodiments, the subject being treated has a baseline GMFM-88 score of greater than 40%. In some embodiments, the subject being treated has a baseline GMFM-88 score of less than 40%.

In some embodiments, administering the recombinant ASA enzyme in accordance with methods disclosed herein results in a smaller decline in motor functions than would be typically observed without the administration. For example, in some embodiments, administering of the recombinant ASA enzyme in accordance with methods of the invention results in decline of the GMFM-88 score by less than 10%, 20%, 30%, 40%, or 50%.

In some embodiments, administering the recombinant ASA enzyme in accordance with methods disclosed herein results in substantial stabilization of motor function, e.g., substantial stabilization of a score such as the GMFM-88 score. By "substantial stabilization" it is meant that there is a lack of decline or worsening over a period of time, e.g., over the treatment period and/or over a period during which decline or worsening would normally be expected in the absence of treatment.

In some embodiments, administering the recombinant ASA enzyme in accordance with methods disclosed herein results in improvement of motor function, e.g., improvement of a score such as the GMFM-88 score.

Biomarkers

In certain embodiments, treatment efficacy comprises alteration(s) in the level(s) of one or more biomarkers, e.g., that accumulates or is decreased in MLD patients.

In some embodiments, provided are methods of treating metachromatic leukodystrophy (MLD) Syndrome comprising a step of administering intrathecally to a subject in need of treatment a recombinant arylsulfatase A (ASA) enzyme at a therapeutically effective dose and an administration interval for a treatment period sufficient to decrease levels of a biomarker that accumulates in MLD to a baseline level of the biomarker.

The biomarker that accumulates in MLD could be, for example, sulfatide, lysosulfatide, or both. In some embodiments, the biomarker is sulfatide. The biomarker can be one that accumulates in one or more bodily tissues and/or one or more bodily fluids in MLD patients. For example, in some embodiments, the biomarker accumulates in a bodily fluid selected from the group consisting of cerebrospinal fluid, urine, blood, and blood serum. In some embodiments, the bodily fluid is cerebrospinal fluid.

In certain embodiments, the baseline sulfatide level in the cerebrospinal fluid in the subject being treated is greater than a certain level, for example, greater than about 0.1 µg/mL, greater than about 0.2 µg/mL, or greater than about 0.3 µg/mL. In some embodiments, the administering of the recombinant ASA enzyme in accordance with methods disclosed herein results in reduction of sulfatide levels in the cerebrospinal fluid, for example by more than about 0.1 µg/mL or more than about 0.2 µg/mL.

In some embodiments, treatment results in decreased sulfatide accumulation in various tissues or body fluids. In some embodiments, treatment results in decreased sulfatide accumulation in brain target tissues, spinal cord neurons, and/or peripheral target tissues. In certain embodiments, sulfatide accumulation is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control or a baseline level. In some embodiments, sulfatide accumulation is decreased by at least 1-fold, 2-fold, 3-fold, 4-fold, 5-fold, 6-fold, 7-fold, 8-fold, 9-fold or 10-fold as compared to a control or a baseline level. It will be appreciated that sulfatide storage may be assessed by any appropriate method. For example, in some embodiments, sulfatide storage is measured by alcian blue staining. In some embodiments, sulfatide storage is measured by LAMP-1 staining.

In some embodiments, provided are methods of treating metachromatic leukodystrophy (MLD) Syndrome comprising a step of administering intrathecally to a subject in need of treatment a recombinant arylsulfatase A (ASA) enzyme at a therapeutically effective dose and an administration interval for a treatment period sufficient to increase levels of a biomarker that is decreased in MLD in a brain tissue relative to a baseline level of the biomarker.

The brain tissue can be any brain tissue where levels of the biomarker are typically decreased in MLD patients, for example, the deep white matter of the brain. Biomarkers that may be useful include certain metabolites, such as N-acetylaspartate. N-acetylaspartate levels can be assessed in brain tissues, for example, by proton magnetic resonance spectroscopy.

Brain Lesion Involvement

In certain embodiments, treatment efficacy comprises a measure related to brain lesion involvement. In certain embodiments, provided are methods of treating metachromatic leukodystrophy (MLD) Syndrome comprising a step of administering intrathecally to a subject in need of treatment a recombinant arylsulfatase A enzyme at a therapeutically effective dose and an administration interval for a treatment period sufficient to stabilize or reduce brain lesion involvement relative to baseline.

Brain lesion involvement can be assessed, for example, by non-invasive methods such as imaging methods. Suitable assessment methods include qualitative, quantitative, and semi-quantitative methods. For example, a non-invasive imaging method for assessing brain lesion involvement in MLD patients is the MLD MRI (magnetic resonance imaging) severity score. (See, e.g., Eichler et al. AJNR Am J Neuroradiol. 2009 November; 30(10):1893-7, the entire contents of which are herein incorporated by reference.) In some embodiments, administering of the recombinant ASA enzyme results in reduction of the MLD MRI severity score in the subject relative to baseline. In some embodiments, administering of the recombinant ASA enzyme results in stabilization of the MLD MRI severity score in the subject relative to baseline.

Additional Measures of Treatment Efficacy

Inventive methods may alternatively or additionally result in one or more other measures of treatment efficacy as discussed herein. In some embodiments, treatment results in reduced vacuolization in neurons (e.g., neurons containing Purkinje cells). In certain embodiments, vacuolization in neurons is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control or to baseline. In some embodiments, vacuolization is decreased by at least 1-fold, 2-fold, 3-fold, 4-fold, 5-fold, 6-fold, 7-fold, 8-fold, 9-fold or 10-fold as compared to a control or to baseline.

In some embodiments, treatment results in increased ASA enzyme activity in various tissues. In some embodiments, treatment results in increased ASA enzyme activity in brain target tissues, spinal cord neurons and/or peripheral target tissues. In some embodiments, ASA enzyme activity is increased by about 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900%, 1000% or more as compared to a control or to baseline. In some embodiments, ASA enzyme activity is increased by at least 1-fold, 2-fold, 3-fold, 4-fold, 5-fold, 6-fold, 7-fold, 8-fold, 9-fold or 10-fold as compared to a control or to baseline. In some embodiments, increased ASA enzymatic activity is at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg, 600 nmol/hr/mg or more. In some embodiments, ASA enzymatic activity is increased in the lumbar region. In some embodiments, increased ASA enzymatic activity in the lumbar region is at least approximately 2000 nmol/hr/mg, 3000 nmol/hr/mg, 4000 nmol/hr/mg, 5000 nmol/hr/mg, 6000 nmol/hr/mg, 7000 nmol/hr/mg, 8000 nmol/hr/mg, 9000 nmol/hr/mg, 10,000 nmol/hr/mg, or more.

In some embodiments, treatment results in decreased progression of loss of cognitive ability. In certain embodiments, progression of loss of cognitive ability is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control or to baseline. In some embodiments, treatment refers to decreased developmental delay. In certain embodiments, developmental delay is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control or to baseline.

In some embodiments, treatment refers to increased survival (e.g. survival time). For example, treatment can result in an increased life expectancy of a patient. In some embodiments, treatment according to the present invention results in an increased life expectancy of a patient by more than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200% or more, as compared to the average life expectancy of one or more control individuals with similar disease without treatment. In some embodiments, treatment according to the present invention results in an increased life expectancy of a patient by more than about 6 month, about 7 months, about 8 months, about 9 months, about 10 months, about 11 months, about 12 months, about 2 years, about 3 years, about 4 years, about 5 years, about 6 years, about 7 years, about 8 years, about 9 years, about 10 years or more, as compared to the average life expectancy of one or more control individuals with similar disease without treatment. In some embodiments, treatment according to the present invention results in long term survival of a patient. As used herein, the term "long term survival" refers to a survival time or life expectancy longer than about 40 years, 45 years, 50 years, 55 years, 60 years, or longer.

The terms, "improve," "increase" or "reduce," as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein. A "control individual" is an individual afflicted with the same form MLD (e.g., late-infantile, juvenile, or adult-onset form), who is about the same age and/or gender as the individual being treated (to ensure that the stages of the disease in the treated individual and the control individual(s) are comparable).

Subjects

The individual (also referred to as "patient" or "subject") being treated is an individual (e.g., fetus, infant, child, adolescent, or adult human) having MLD or having the potential to develop MLD (i.e., at risk of developing MLD).

In many embodiments, the subject is a mammal, for example, a human.

In some embodiments, the subject is sixteen years old or younger, e.g., twelve years old or younger, nine years old or younger, six years old or younger, four years old or younger, three years old or younger, two years old or younger, 18 months or younger, 12 months or younger, or 6 months or younger.

Subjects may have any of the forms of MLD—e.g., adult form, juvenile form, or late infantile form.

Subjects may or may not be exhibiting at least one symptom of MLD as discussed herein at the time of commencement of treatment.

Subjects may or may not be diagnosed with MLD at the time of commencement of treatment. For example, in some embodiments, the subject has not been identified as being at risk of developing MLD. Thus, methods of treatment can The individual can have residual endogenous ASA expression and/or activity, or no measurable activity. For example, the individual having MLD may have ASA expression levels that are less than about 30-50%, less than about 25-30%, less than about 20-25%, less than about 15-20%, less than about 10-15%, less than about 5-10%, less than about 0.1-5% of normal ASA expression levels.

In some embodiments, the individual is an individual who has been recently diagnosed with the disease. Typically, early treatment (treatment commencing as soon as possible after diagnosis) is important to minimize the effects of the disease and to maximize the benefits of treatment.

Immune Tolerance

Generally, intrathecal administration of a therapeutic agent (e.g., a replacement enzyme) according to the present invention does not result in severe adverse effects in the subject. As used herein, severe adverse effects induce, but are not limited to, substantial immune response, toxicity, or death. As used herein, the term "substantial immune response" refers to severe or serious immune responses, such as adaptive T-cell immune responses.

Thus, in many embodiments, inventive methods according to the present invention do not involve concurrent immunosuppressant therapy (i.e., any immunosuppressant therapy used as pre-treatment/pre-conditioning or in parallel to the method). In some embodiments, inventive methods according to the present invention do not involve an immune tolerance induction in the subject being treated. In some embodiments, inventive methods according to the present invention do not involve a pre-treatment or preconditioning of the subject using T-cell immunosuppressive agent.

In some embodiments, intrathecal administration of therapeutic agents can mount an immune response against these agents. Thus, in some embodiments, it may be useful to render the subject receiving the replacement enzyme tolerant to the enzyme replacement therapy. Immune tolerance may be induced using various methods known in the art. For example, an initial 30-60 day regimen of a T-cell immunosuppressive agent such as cyclosporin A (CsA) and an antiproliferative agent, such as, azathioprine (Aza), combined with weekly intrathecal infusions of low doses of a desired replacement enzyme may be used.

Any immunosuppressant agent known to the skilled artisan may be employed together with a combination therapy of the invention. Such immunosuppressant agents include but are not limited to cyclosporine, FK506, rapamycin, CTLA4-Ig, and anti-TNF agents such as etanercept (see e.g. Moder, 2000, Ann. Allergy Asthma Immunol. 84, 280-284; Nevins, 2000, Curr. Opin. Pediatr. 12, 146-150; Kurlberg et al., 2000, Scand. J. Immunol. 51, 224-230; Ideguchi et al., 2000, Neuroscience 95, 217-226; Potter et. al., 1999, Ann. N.Y. Acad. Sci. 875, 159-174; Slavik et al., 1999, Immunol. Res. 19, 1-24; Gaziev et al., 1999, Bone Marrow Transplant. 25, 689-696; Henry, 1999, Clin. Transplant. 13, 209-220; Gummert et al., 1999, J. Am. Soc. Nephrol. 10, 1366-1380; Qi et al., 2000, Transplantation 69, 1275-1283). The anti-IL2 receptor (.alpha.-subunit) antibody daclizumab (e.g. Zenapax.TM.), which has been demonstrated effective in transplant patients, can also be used as an immunosuppressant agent (see e.g. Wiseman et al., 1999, Drugs 58, 1029-1042; Beniaminovitz et al., 2000, N. Engl J. Med. 342, 613-619; Ponticelli et al., 1999, Drugs R. D. 1, 55-60; Berard et al., 1999, Pharmacotherapy 19, 1127-1137; Eckhoff et al., 2000, Transplantation 69, 1867-1872; Ekberg et al., 2000, Transpl. Int. 13, 151-159). Additional immunosuppressant agents include but are not limited to anti-CD2 (Branco et al., 1999, Transplantation 68, 1588-1596; Przepiorka et al., 1998, Blood 92, 4066-4071), anti-CD4 (Marinova-Mutafchieva et al., 2000, Arthritis Rheum. 43, 638-644; Fishwild et al., 1999, Clin. Immunol. 92, 138-152), and anti-CD40 ligand (Hong et al., 2000, Semin. Nephrol. 20, 108-125; Chirmule et al., 2000, J. Virol. 74, 3345-3352; Ito et al., 2000, J. Immunol. 164, 1230-1235).

Administration

Inventive methods of the present invention contemplate single as well as multiple administrations of a therapeutically effective amount of the therapeutic agents (e.g., replacement enzymes) described herein. Therapeutic agents (e.g., replacement enzymes) can be administered at regular intervals, depending on the nature, severity and extent of the subject's condition (e.g., a lysosomal storage disease). In some embodiments, a therapeutically effective amount of the therapeutic agents (e.g., replacement enzymes) of the present invention may be administered intrathecally periodically at regular intervals (e.g., once every year, once every six months, once every five months, once every three months, bimonthly (once every two months), monthly (once every month), biweekly (once every two weeks), weekly).

In some embodiments, intrathecal administration may be used in conjunction with other routes of administration (e.g., intravenous, subcutaneously, intramuscularly, parenterally, transdermally, or transmucosally (e.g., orally or nasally)). In some embodiments, those other routes of administration (e.g., intravenous administration) may be performed no more frequent than biweekly, monthly, once every two months, once every three months, once every four months, once every five months, once every six months, annually administration.

As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). For example, a therapeutically effective amount may be an amount sufficient to achieve a desired therapeutic and/or prophylactic effect, such as an amount sufficient to modulate lysosomal enzyme receptors or their activity to thereby treat such lysosomal storage disease or the symptoms thereof (e.g., a reduction in or elimination of the presence or incidence of "zebra bodies" or cellular vacuolization following the administration of the compositions of the present invention to a subject). Generally, the amount of a therapeutic agent (e.g., a recombinant lysosomal enzyme) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

In some embodiments, a therapeutically effective dose is or greater than about 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg or 100 mg. In particular embodiments, a therapeutically effective dose is or is greater than about 10 mg. In particular embodiments, a therapeutically effective dose is or is greater than about 30 mg. In particular embodiments, a therapeutically effective dose is or is greater than about 100 mg. In some embodiments, a therapeutically effective dose is less than about 500 mg, 450 mg, 400 mg, 350 mg, 300 mg, 250 mg, or 200 mg. In particular embodiments, a therapeutically effective dose is less than about 200 mg. In some embodiments, a therapeutically effective dose ranges between about 1-100 mg, about 5-100 mg, about 10-90 mg, about 10-80 mg, about 5-70 mg, about 5-60 mg, about 5-60 mg, about 10-100 mg, about 10-90 mg, about 10-80 mg, about 10-70 mg, about 10-60 mg, or about 10-50 mg. In some embodiments, a therapeutically effective dose ranges between about 100 mg and about 200 mg.

In some embodiments, the therapeutically effective dose ranges from about 0.005 mg/kg brain weight to 500 mg/kg brain weight, e.g., from about 0.005 mg/kg brain weight to 400 mg/kg brain weight, from about 0.005 mg/kg brain weight to 300 mg/kg brain weight, from about 0.005 mg/kg brain weight to 200 mg/kg brain weight, from about 0.005 mg/kg brain weight to 100 mg/kg brain weight, from about 0.005 mg/kg brain weight to 90 mg/kg brain weight, from about 0.005 mg/kg brain weight to 80 mg/kg brain weight, from about 0.005 mg/kg brain weight to 70 mg/kg brain weight, from about 0.005 mg/kg brain weight to 60 mg/kg brain weight, from about 0.005 mg/kg brain weight to 50 mg/kg brain weight, from about 0.005 mg/kg brain weight to 40 mg/kg brain weight, from about 0.005 mg/kg brain weight to 30 mg/kg brain weight, from about 0.005 mg/kg brain weight to 25 mg/kg brain weight, from about 0.005 mg/kg brain weight to 20 mg/kg brain weight, from about 0.005 mg/kg brain weight to 15 mg/kg brain weight, from about 0.005 mg/kg brain weight to 10 mg/kg brain weight.

In some embodiments, the therapeutically effective dose is greater than about 0.1 mg/kg brain weight, greater than about 0.5 mg/kg brain weight, greater than about 1.0 mg/kg brain weight, greater than about 3 mg/kg brain weight, greater than about 5 mg/kg brain weight, greater than about 10 mg/kg brain weight, greater than about 15 mg/kg brain weight, greater than about 20 mg/kg brain weight, greater than about 30 mg/kg brain weight, greater than about 40 mg/kg brain weight, greater than about 50 mg/kg brain weight, greater than about 60 mg/kg brain weight, greater than about 70 mg/kg brain weight, greater than about 80 mg/kg brain weight, greater than about 90 mg/kg brain weight, greater than about 100 mg/kg brain weight, greater than about 150 mg/kg brain weight, greater than about 200 mg/kg brain weight, greater than about 250 mg/kg brain weight, greater than about 300 mg/kg brain weight, greater than about 350 mg/kg brain weight, greater than about 400 mg/kg brain weight, greater than about 450 mg/kg brain weight, greater than about 500 mg/kg brain weight.

In some embodiments, the therapeutically effective dose may also be defined by mg/kg body weight. As one skilled in the art would appreciate, the brain weights and body weights can be correlated. Dekaban AS. "Changes in brain weights during the span of human life: relation of brain weights to body heights and body weights," Ann Neurol 1978; 4:345-56. Thus, in some embodiments, the dosages can be converted as shown in Table 4.

TABLE 4

Correlation between Brain Weights, body weights and ages of males

| Age (year) | Brain weight (kg) | Body weight (kg) |
|---|---|---|
| 3 (31-43 months) | 1.27 | 15.55 |
| 4-5 | 1.30 | 19.46 |

In some embodiments, the therapeutically effective dose may also be defined by mg/15 cc of CSF. As one skilled in the art would appreciate, therapeutically effective doses based on brain weights and body weights can be converted to mg/15 cc of CSF. For example, the volume of CSF in adult humans is approximately 150 mL (Johanson C E, et al. "Multiplicity of cerebrospinal fluid functions: New challenges in health and disease," Cerebrospinal Fluid Res. 2008 May 14; 5:10). Therefore, single dose injections of 0.1 mg to 50 mg protein to adults would be approximately 0.01 mg/15 cc of CSF (0.1 mg) to 5.0 mg/15 cc of CSF (50 mg) doses in adults.

It is to be further understood that for any particular subject, specific dosage regimens should be adjusted over time according to the individual need and the professional judgment of the person administering or supervising the administration of the enzyme replacement therapy and that dosage ranges set forth herein are exemplary only and are not intended to limit the scope or practice of the claimed invention.

In certain embodiments, recombinant arylsulfatase A enzyme is administered at an administration interval, e.g., a regular interval. For example, the administration interval can be once a week, once every two weeks, or once a month.

In certain embodiments, recombinant arylsulfatase A enzyme is administered for a treatment period. The treatment period can be predetermined or it can be adjusted depending on the patient's response to the treatment, including, but not limited to, possible adverse symptoms and/or evidence of treatment efficacy as discussed herein. For example, the treatment period can be at least 6 months, at least 9 months, at least 12 months, at least 24 months, or even greater.

It is contemplated that in some embodiments, subjects will undergo treatment over a certain treatment period, undergo a certain period during which they receive no treatment or an alternative treatment, and then undergo again another treatment period.

Kits

The present invention further provides kits or other articles of manufacture which contains the formulation of the present invention and provides instructions for its reconstitution (if lyophilized) and/or use. Kits or other articles of manufacture may include a container, an IDDD, a catheter and any other articles, devices or equipment useful in interthecal administration and associated surgery. Suitable containers include, for example, bottles, vials, syringes (e.g., pre-filled syringes), ampules, cartridges, reservoirs, or lyojects. The container may be formed from a variety of materials such as glass or plastic. In some embodiments, a container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, the container may holds formulations and a label on, or associated with, the container that may indicate directions for reconstitution and/or use. For example, the label may indicate that the formulation is reconstituted to protein concentrations as described above. The label may further indicate that the formulation is useful or intended for, for example, IT administration. In some embodiments, a container may contain a single dose of a stable formulation containing a therapeutic agent (e.g., a replacement enzyme). In various embodiments, a single dose of the stable formulation is present in a volume of less than about 15 ml, 10 ml, 5.0 ml, 4.0 ml, 3.5 ml, 3.0 ml, 2.5 ml, 2.0 ml, 1.5 ml, 1.0 ml, or 0.5 ml. Alternatively, a container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final protein concentration in the reconstituted formulation will generally be at least 1 mg/ml (e.g., at least 5 mg/ml, at least 10 mg/ml, at least 25 mg/ml, at least 50 mg/ml, at least 75 mg/ml, at least 100 mg/ml). In some embodiments, the final protein concentration is at least 25 mg/mL, for example, 30 mg/mL. Kits or other articles of manufacture may further include other materials desirable from a commercial and user standpoint, including other buffers, diluents, filters, needles, IDDDs, catheters, syringes, and package inserts with instructions for use.

The invention will be more fully understood by reference to the following examples. They should not, however, be construed as limiting the scope of the invention. While certain compounds, compositions and methods described herein have been described with specificity in accordance with certain embodiments, the following examples serve only to illustrate the compounds of the invention and are not intended to limit the same. All literature citations are incorporated by reference.

EXAMPLES

Example 1: Intrathecal Administration of Recombinant Arylsulfatase a is Safe and Improves Symptoms in Human Late Infantile and Juvenile Metachromatic Leukodystrophy Patients Clinical forms of metachromatic leukodystrophy are typically divided by the age of onset, with late infantile metachromatic leukodystrophy being the associated with an age of onset of three years or younger, juvenile metachromatic leukodystrophy being associated with an age of onset of between four and sixteen years of age, and adult metachromatic leukodystrophy being associated with an age of onset of greater than sixteen years of age.

Children with metachromatic leukodystrophy typically experience a decline in motor function, and those with late-infantile metachromatic leukodystrophy have only a roughly 52% five-year survival rate (Mahmood A et al. J Child Neurol. 2010; 25:572-80). There are currently no approved pharmacological treatments.

The present Example describes a phase 1/2, non-randomized, open-label dose-escalation clinical study to evaluate the safety and efficacy of recombinant human arylsulfatase A (ASA) in children with Metachromatic Leukodystrophy (MLD), e.g., having either late-infantile or juvenile metachromatic leukodystrophy. To evaluate efficacy, the effect of recombinant human ASA treatment on gross motor function, brain lesion involvement, and sulfatide levels in the CSF were analyzed.

Eighteen male or female patients were enrolled in the study and met all of the following screening criteria: MLD diagnosis confirmed by ASA deficiency (by assay in leukocytes) and elevated sulfatide levels in patient urine; appearance of first disease symptoms at or before 30 months of age; ambulatory at the time of screening (e.g., a minimum level of function required, defined as the ability to stand up and walk forward 10 steps with one hand held); less than twelve years of age at the time of enrollment; and neurologic signs of MLD present at the screening examination.

The exclusion criteria included: history of hematopoietic stem cell transplantation; any known or suspected hypersensitivity to anesthesia or unacceptably high risk of anesthesia due to airway compromise or other conditions; any other medical condition, serious intercurrent illness, or extenuating circumstance that would preclude participation in the study. The study design is shown in FIG. 1.

Upon enrollment, patients were screened to assess their eligibility based on the criteria outlined above as well as to obtain informed consent. Presurgical safety assessments were also made for surgical implantation of the IDDD. Standard hospital procedures for surgery were followed.

Patients were enrolled in one of three escalating dose cohorts (n=6 patients per cohort, at 10 mg, 30 mg, or 100 mg per dose) of intrathecally administered recombinant human ASA. Patients received sedation as-needed at the discretion of the administrator. Any escalation of newly included patients to the next dose level was based on review of the safety data obtained for patients in the lower dose cohort by an independent Data Safety Monitoring Board and representatives from Shire Human Genetic Therapies, and only after patients received at least two doses. Table 5 shows the patient demographics for the study.

TABLE 5

| Characteristic | | 10 mg rhASA (n = 6) | 30 mg rhASA (n = 6) | 100 mg rhASA (n = 6) |
|---|---|---|---|---|
| Age at enrollment, months | Mean ± standard deviation | 31.5 ± 11.5 | 47.3 ± 20.2 | 52.3 ± 31.1 |
| | Range | 23-54 | 31-81 | 23-107 |
| Boys, n | | 3 | 3 | 5 |
| Ethic origin, n | White | 5 | 4 | 2 |
| | Asian | 0 | 0 | 4 |
| | Other | 1 | 2 | 0 |

Briefly, a port was placed subcutaneously over a rib with a catheter to the spinal channel at the lumbar level. If the device became nonfunctional at any time, it was removed and replaced. Either the PORT-A-CATH II® or the SOPH-A-PORT® Mini S used, the latter of which appeared to be better tolerated. (See Table 6.) A series of CSF assessments were made at baseline and each study visit in a predose manner. Recombinant human ASA was dosed via the implanted IDDD every other week for 38 weeks (beginning with week 0) for a total of 20 injections. The IDDD was used for both CSF sampling and recombinant human ASA injections. Samples for measurements to assess safety/efficacy were taken every other week before dosing.

Safety

Table 6 lists adverse events reported in the study, with the numbers shown representing the number of patients. As shown in Table 6, there were no serious treatment-related adverse events, deaths, or discontinuations in any of the three cohorts (10 mg, 30 mg, or 100 mg dosing).

TABLE 6

| Event reported | 10 mg rhASA (n = 6) | 30 mg rhASA (n = 6) | 100 mg rhASA (n = 6) |
|---|---|---|---|
| Any AdverseEvent (AE) | 6 | 6 | 6 |
| Any IDDD-related AE | 3 | 3 | 4 |
| Death | 0 | 0 | 0 |
| Discontinuation due to AEs | 0 | 0 | 0 |
| Any serious AE[a] | 5 | 4 | 4 |
| Any treatment-related AE[a] | 3 | 4 | 4 |
| Blood and lymphatic system disorders | 0 | 2 | 0 |
| General disorders and administration site conditions | 3 | 1 | 0 |
| Investigations (clinical laboratory results)[b] | 3 | 1 | 1 |
| Skin and subcutaneous tissue disorders | 2 | 2 | 0 |

[a]Events by system organ class are shown when occurring in at least two patients in any group.
[b]Include increased alanine aminotransferase, blood pressure, eosinophil count, and γ-glutamyltransferase.
AE = adverse events;
IDDD = intrathecal drug-delivery device;
rhASA = recombinant human arylsulfatase A

TABLE 7

| | PORT-A-CATH II® | | SOPH-A-PORT® |
|---|---|---|---|
| IDDD-related serious AE | 10 mg rhASA (n = 6) | 30 mg rhASA (n = 5)[a] | Mini S 100 mg rhASA (n = 6) |
| Device failure | 2 | 0 | 1 |
| Device dislocation | 1 | 1 | 0 |
| Device malfunction | 1 | 0 | 0 |
| Device occlusion | 1 | 0 | 0 |
| Implant site effusion | 1 | 0 | 1 |
| Implant site infection | 0 | 0 | 1 |

TABLE 7-continued

| | PORT-A-CATH II® | | SOPH-A-PORT® |
|---|---|---|---|
| IDDD-related serious AE | 10 mg rhASA (n = 6) | 30 mg rhASA (n = 5)[a] | Mini S 100 mg rhASA (n = 6) |
| Number of patients | ≥1 IDDD-related serious AE reported by four patients | | All IDDD-related serious AEs reported by one patient |

[a]One patient had the SOPH A-PORT® Mini S implanted at the start of the study.
AE = adverse events;
IDDD = intrathecal drug-delivery device;
rhASA = recombinant human arylsulfatase A Motor Function Motor function was assessed by the Gross Motor Function Measure-88 (GMFM-88), a clinical tool designed to quantify changes in gross motor function in children. Items on the GMFM-88 include activities involving lying, rolling, walking, running and jumping skills.

Figure 2:
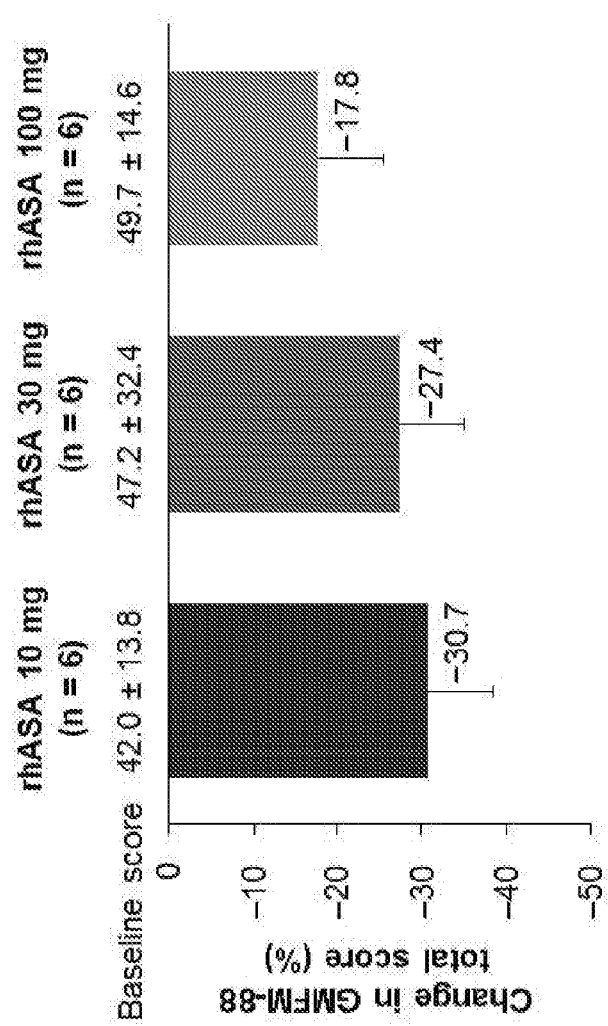
FIG. 2 shows the change in Gross Motor Function Measure-88 (GMFM-88) total score (from baseline) as a percentage in each of the three treatment groups (10 mg, 30 mg, and 100 mg rhASA) at week 40 of the phase 1/2 clinical study described in Example 1. The data shown are least-squares mean; the error bars represent standard error. The baseline data are presented as mean±standard deviation. Comparisons between groups were analyzed by analysis of covariance (ANCOVA) with changes from baseline in GMFM-88 score as the dependent variable and dose-group and baseline value as covariates.

Changes in GMFM-88 total score across all treatment groups at week 40 are shown in FIG. 2. At week 40, motor function decline was numerically lower in the patient group administered 100 mg than with the other (lower doses), although no statistically significant differences were detected between groups.

Figure 3:
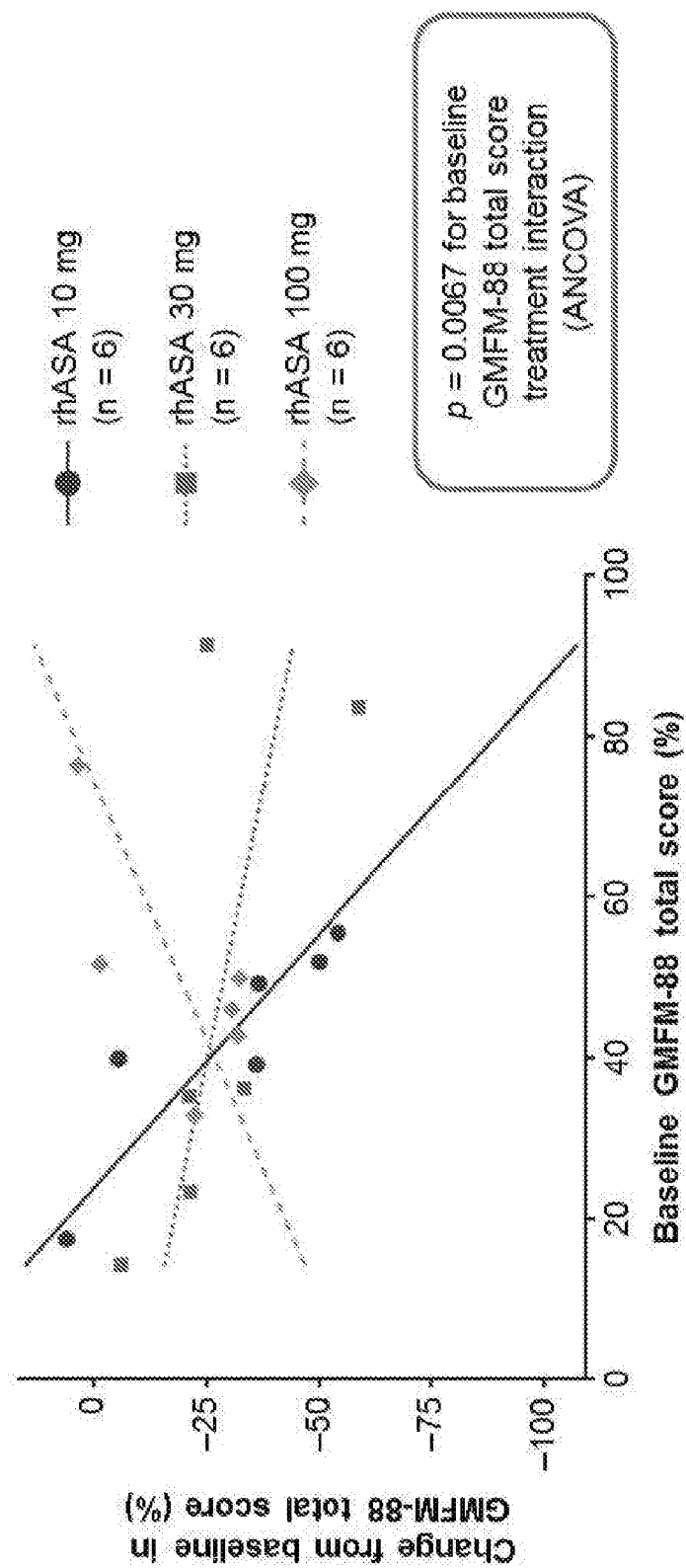
FIG. 3 shows the treatment effect (as measured by change from baseline in the GMFM-88 total score (%)) versus baseline GMFM-88 total score (%) in patients from the clinical study described in Example 1. Circles: 10 mg rhASA; squares: 30 mg rhASA; diamonds: 100 mg rhASA.
Figure 4:
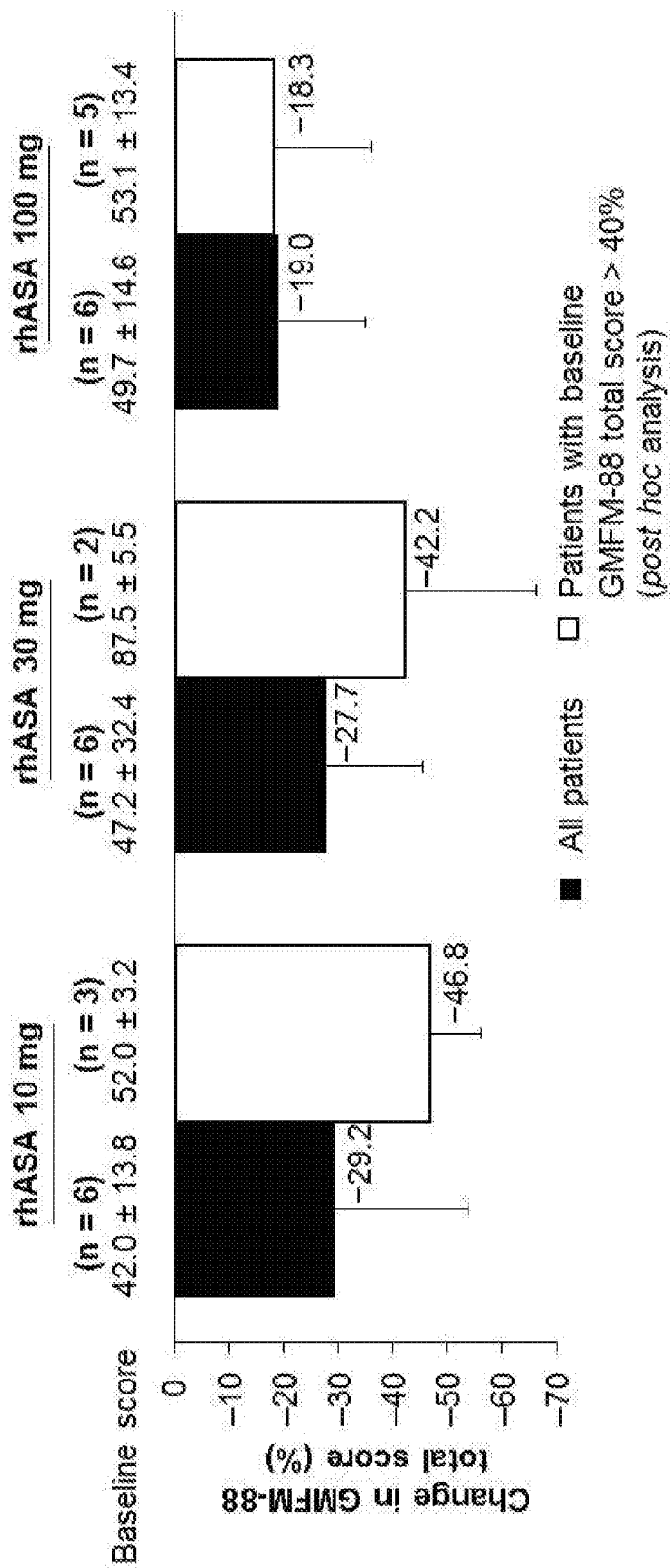
FIG. 4 shows the change in GMFM-88 total score (%) in all treatment groups in the clinical study described in Example 1, with values for those patients having GMFM-88 baseline total scores of greater than 40% displayed in separate bars. Black solid bars show data for all patients, while white solid bars show data only for patients with baselines GMFM-88 total scores of greater than 40%. Data in the figures are presented as means, with error bars indicating standard deviations. Baseline data are presented as mean±standard deviation.

However, a statistically significant interaction between baseline GMFM-88 total score and treatment effect (as assessed by change in GMFM-88 score from baseline) was detected (p=0.0067 by ANCOVA (analysis of covariance); see FIG. 3). At week 40, among children with GMFM-88 baseline total scores of greater than 40%, there was less motor function decline in those children treated with 100 mg rhASA than in the other groups. (See FIG. 4.)

Brain Lesion Involvement

The metachromatic leukodystrophy magnetic resonance imaging (MLD MRI) severity score is a quantitative measure of brain lesion involvement. (See, e.g., Eichler et al. AJNR Am J Neuroradiol. 2009 November; 30(10):1893-7.) MRI data were assessed in patients at week 40 in a blinded fashion by one investigator.

Figure 5:
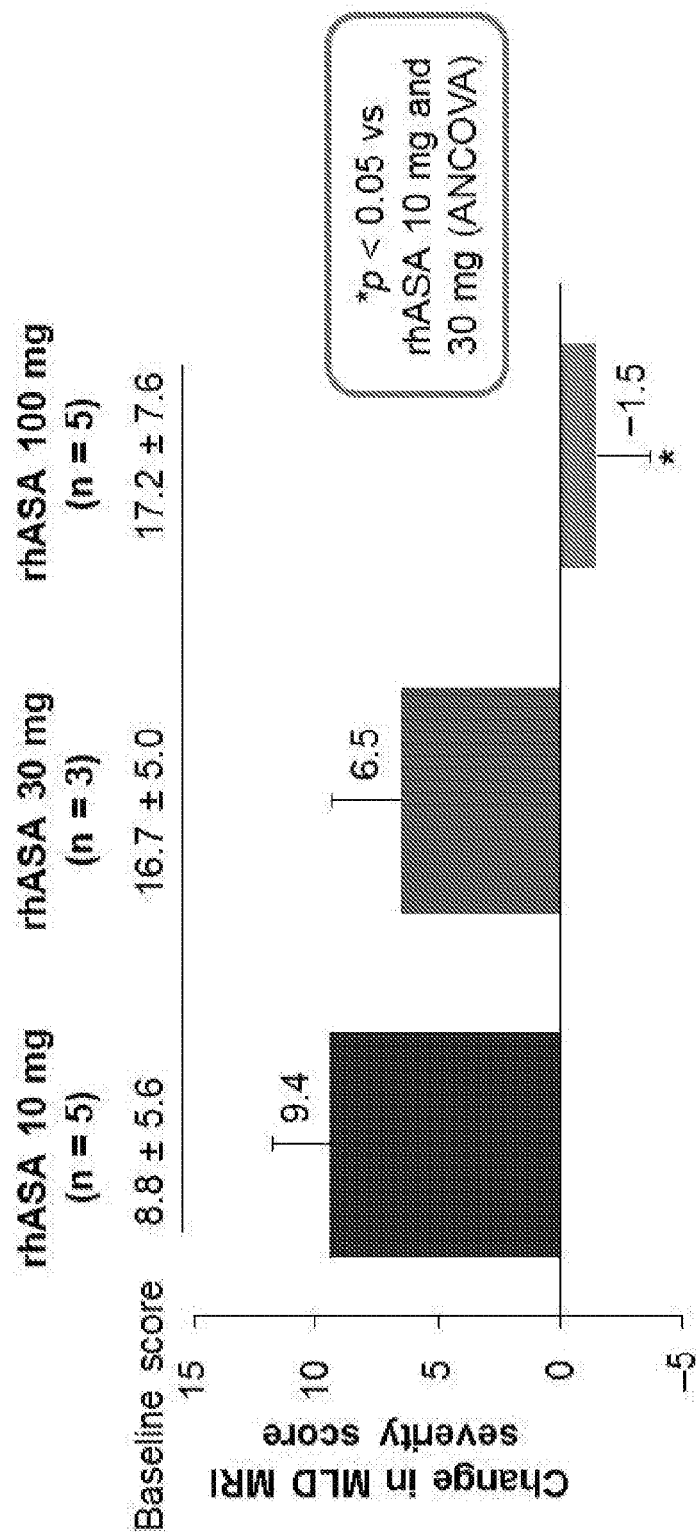
FIG. 5 shows the change metachromatic leukodystrophy magnetic resonance imaging (MRI) severity score at week 40 in patients enrolled in the clinical study described in Example 1. The data shown are least-squares means; the error bars represent standard error. Baseline data are presented as mean±standard deviation. Unbalanced baseline values were adjusted for by using least-squares mean.

As shown in FIG. 5, at week 40 the MLD MRI severity score appeared stable in the 100 mg cohort, which exhibited a slight decrease in the score. The MLD MRI severity score change in the 100 mg cohort was significantly different than the changes observed in the 10 mg and 30 mg cohorts, which exhibited increases in MLD MRI severity scores over the course of treatment.

Sulfatide Levels in the Cerebrospinal Fluid

Figure 6:
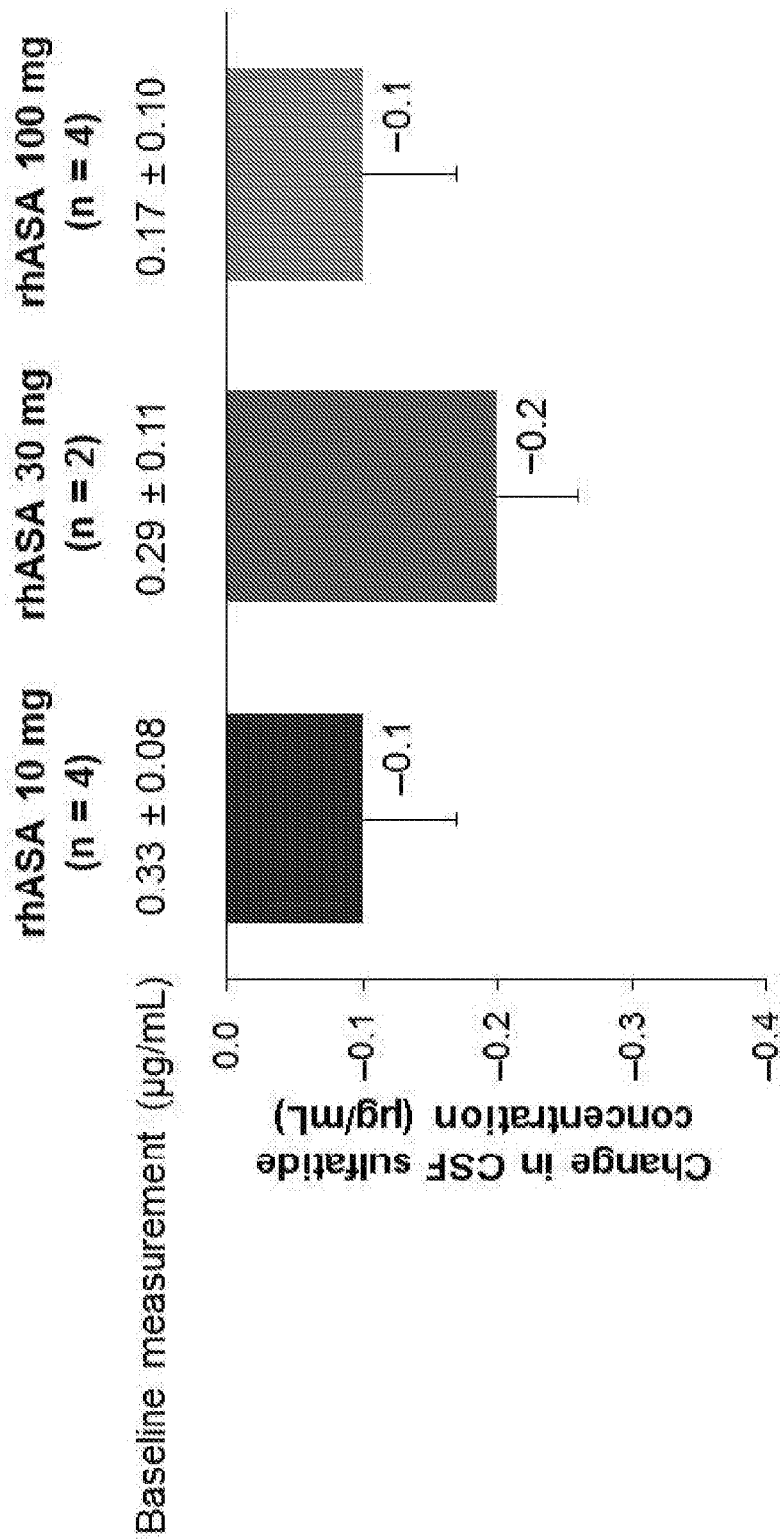
FIG. 6 shows sulfatide levels in the cerebrospinal fluid at week 40 in patients enrolled in the clinical study described in Example 1. The data shown are presented as means; error bars represent standard deviation. Baseline data are presented as mean±standard deviation.

Concentrations of sulfatide, a metabolite that accumulates in metachromatic leukodystrophy patients, were studied in the cerebrospinal fluid of patients. As shown in FIG. 6, small reductions in sulfatide concentrations were observed in all cohorts at week 40.

Discussion

The results described in this example demonstrate that intrathecal administration of recombinant human ASA in patients with MLD has an acceptable safety profile and stabilizes and/or slows the progression of the disease. As no treatments are currently available for this progressive, and ultimately fatal, disease, intrathecal administration of recombinant human ASA represents an promising approach for the treatment of MLD.

Example 2: Additional Safety and Efficacy Assessments of Recombinant Arylsulfatase a for the Treatment of Metachromatic Leukodystrophy Patients with late infantile or juvenile metachromatic leukodystrophy are enrolled in a clinical study whose design and inclusion and exclusion criteria are similar to that described in Example 1. To further assess the safety of recombinant human ASA at particular doses, patients are examined physically and neurologically and their vital signs are monitored. In addition, a battery of analyses including urinalysis, blood serum chemistry, serum sulfatide levels, complete blood count, routine and biomarker analyses of cerebrospinal fluid, and electrocardiology, is performed. Furthermore, anti-rhASA antibody concentrations and/or metabolite (e.g., sulfatide, lyo-sulfatide, and/or N-acetylasparate) levels are measured in various fluids, such as cerebrospinal fluid, urine, and blood. Metabolite levels can also be assessed in the deep white matter of the brain by proton magnetic resonance spectroscopy.

To assess efficacy, one or more of changes in the GMFM-88 score from baseline, motor nerve conduction indicators (such as nerve conduction velocity, compound motor action potential, and distal latency), sensory nerve conduction indicators (such as nerve conduction velocity, amplitude, and distal latency), magnetic resonance imaging and/or magnetic resonance spectroscopy to detect MLD-related abnormalities, somatosensory evoked potentials, functional endoscopic evaluation of swelling, and brainstem auditory evoked response are assessed.

Example 3: Decrease in Cerebrospinal Fluid Sulfatide Levels Over Time

Figure 7:
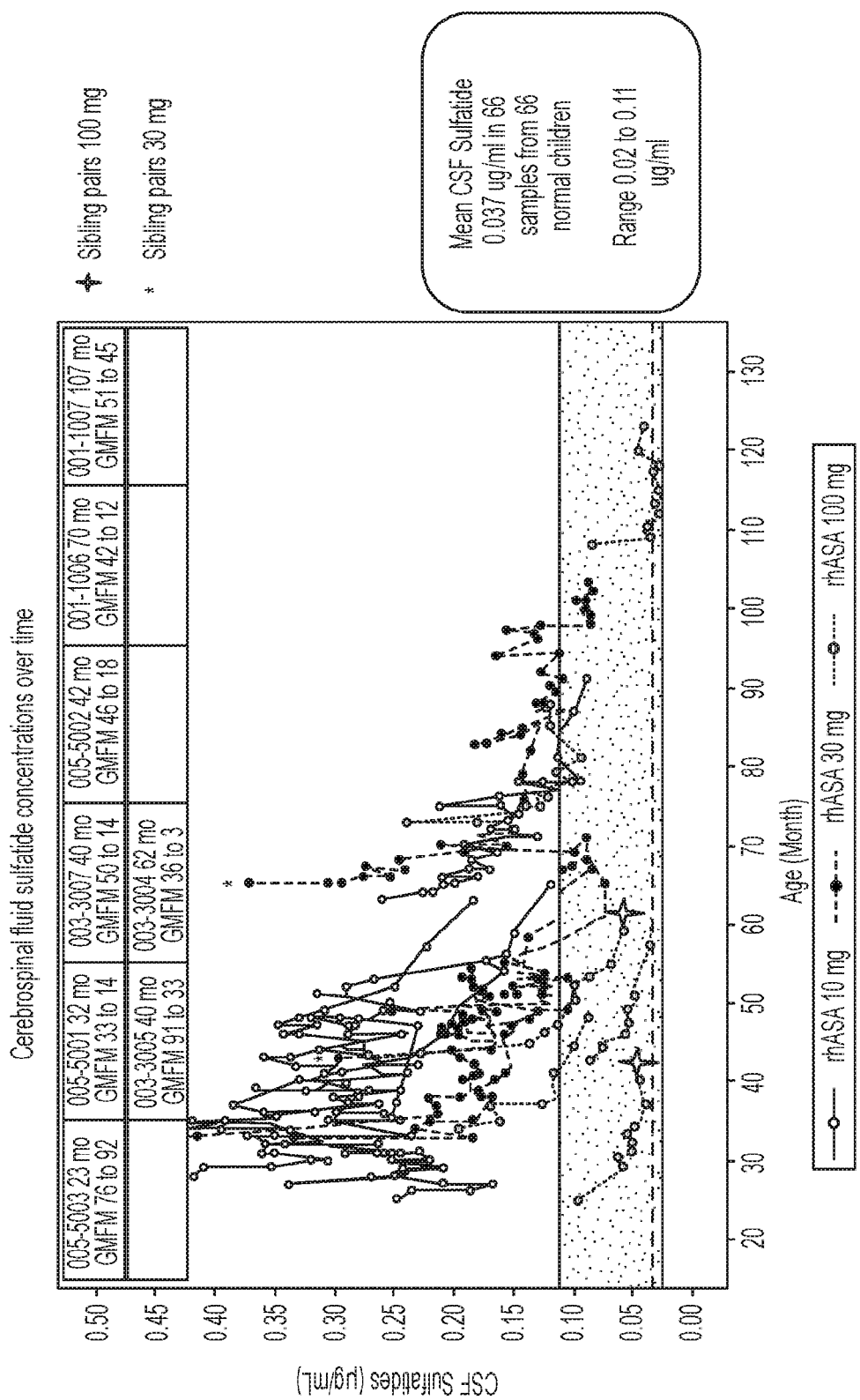
FIG. 7 shows sulfatide levels (in µg/ml) in the cerebrospinal fluid over time by cohort in patients enrolled in a clinical study. The data include data from at least two sibling pairs. Data are shown for patients administered 10 mg, 30 mg, and 100 mg recombinant human arylsulfatase A.

Children were enrolled in a clinical study and administered 10 mg, 30 mg, or 100 mg recombinant human arylsulfatase A by intrathecal administration every other week for 40 weeks. FIG. 7 presents data from some of the children by cohort, and includes data from two sibling pairs (one pair at a 30 mg dose and another pair at a 100 mg dose). As shown in FIG. 7, there was a general trend over time of decreasing sulfatide levels in the cerebrospinal fluid especially apparent in the children given 30 mg and 100 mg doses. Moreover, in children administered 100 mg of recombinant human arylsulfatase A, the sulfatide levels eventually declined such that they were within the upper limit of normal ranges.

Example 4: Intrathecally Delivered rhASA was Well Tolerated for Over 104 Weeks

Figure 8:
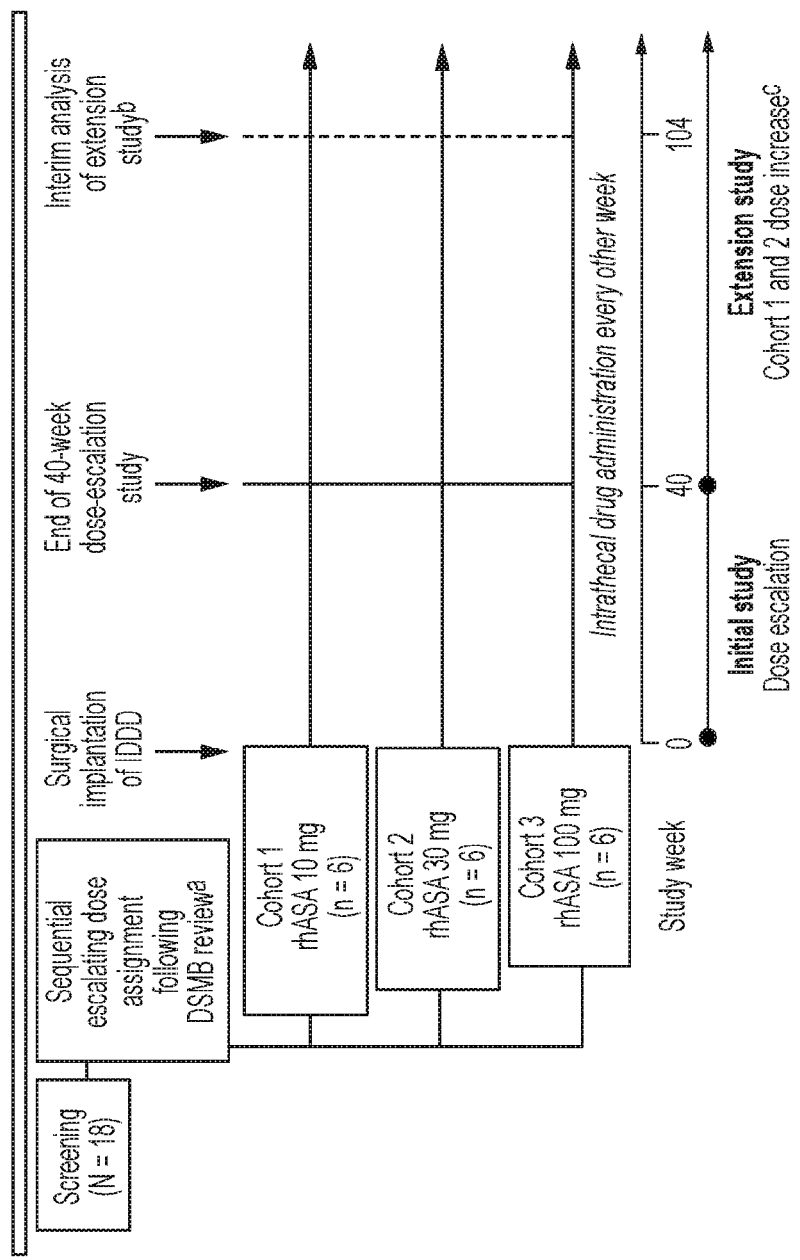
FIG. 8 illustrates the design of a phase 1/2, open-label, non-controlled, long term extension clinical study of intrathecally delivered recombinant human arylsulfatase A in children with Metachromatic Leukodystrophy (MLD).

The three cohorts described in Examples 1-3 were eligible for a long-term extensions study which included analysis of safety and other outcome assessments up to week 104 (including the initial 40-week dose escalation study (FIG. 8)). Children with MLD were eligible for enrollment into the initial 40-week study if they were younger than 12 years of age; the appearance of their first MLD symptoms was at or before 30 months of age; and at screening, they could walk 10 steps with one hand held. Eligible patients were sequentially enrolled into one of three escalating dose cohorts (cohort 1, rhASA 10 mg; cohort 2, rhASA 30 mg; cohort 3, rhASA 100 mg). Each patient was surgically implanted with an intrathecal drug delivery device (IDDD) before receiving their first dose. Eleven patients in the early part of the study were implanted with the PORT-A-CATH II (Smiths Medical ASD, Inc., St Paul, Minn., USA) and eight patients were implanted with the SOPH-A-PORT MiniS (Sophysa, Orsay, France) (including one patient who transitioned to this device after originally being implanted with the PORT-A-CATH II).

Children received intrathecal injections of rhASA every 2 weeks. Following the initial 40-week study, the rhASA dose was individually increased in cohorts 1 and 2 (cohort 1, stepwise), with all patients ultimately receiving rhASA 100 mg in the ongoing study. The decision to proceed with escalation to a higher dose was based on a Data Safety Monitoring Board review after patients had received at least two doses of the previous dose. The primary outcome assessment was the safety of rhASA and the IDDD. Other key outcomes assessed at 104 weeks included change in motor function, evaluated using the Gross Motor Function Measure-88 (GMFM-88) total score (range 0-100%); change in MLD severity, evaluated using magnetic resonance imaging (MRI) and a similar scoring method to Eichler et al. (range 0-34, with a higher score indicating greater disease severity) (See, e.g., Eichler et al. AJNR Am J Neuroradiol. 2009 November; 30(10):1893-7); change in the levels of N-acetylaspartate (NAA) in the white matter of the brain, evaluated by magnetic resonance spectroscopy and change in sulfatide concentration in the cerebrospinal fluid (CSF). Table 8 shows the patient demographics for the study.

TABLE 8

| Patient Demographics | | | |
| --- | --- | --- | --- |
| Characteristic | Cohort 1 (n = 6) | Cohort 2 (n = 6) | Cohort 3 (n = 6) |
| Age at enrollment, months | 31.5 ± 11.5 (26.5, 23-54) | 47.3 ± 20.2 (39.5, 31-81) | 52.3 ± 31.1 (41.0, 23-107) |
| Boys, n | 3 | 3 | 5 |
| Ethnic origin, n[a] | | | |
| White | 5 | 4 | 2 |
| Asian | 0 | 0 | 4 |
| Other | 1 | 2 | 0 |
| Age at MLD symptom onset, months | 17.3 ± 7.1 (17.0, 6-27) | 23.3 ± 3.3 (24.0, 18-28) | 24.0 ± 4.5 (24.5, 16-30) |
| Duration of treatment, weeks[b] | 137.2 ± 63.5 (159.9, 28.3c-195.9) | 134.7 ± 12.2 (128.9, 122.1-150.1) | 111.2 ± 5.2 (110.6, 106.1-117.1) |

Data for age at enrollment, age of symptom onset and duration of exposure are shown as mean ± standard deviation (median, range).
[a]Children were enrolled in five countries: France (n = 7), Denmark (n = 4), Australia (n = 3), Germany (n = 2) and Brazil (n = 2). Two patients from Australia relocated to Japan during the extension study.
[b]The time from administration of the first dose to administration of the last dose of rhASA administered.
cOne child withdrew during the 40-week dose-escalation study owing to lack of efficacy.
MLD, metachromatic leukodystrophy;
rhASA, recombinant human arylsulfatase A.

Safety

A summary of recorded adverse events (AEs) up to 104 weeks is presented in Table 9. Eleven patients experienced at least one IDDD-related AE and 14 patients experienced at least one serious AE (SAE). Six patients experienced at least one IDDD-related SAE. Thirteen patients experienced at least one AE that was judged by the investigators to be related to the study treatment, most frequently pyrexia (n=6).

TABLE 9

Summary of adverse events up to 104 weeks

| Event reported | Cohort 1 (n = 6) | Cohort 2 (n = 6) | Cohort 3 (n = 6) |
| --- | --- | --- | --- |
| ANY AE | 6 | 6 | 6 |
| Any IDDD-related AE | 5 | 2 | 4 |
| Death | 0 | 1 | 0 |
| Discontinuation due to AEs | 0 | 0 | 0 |
| Any SAE[a] | 5 | 5 | 4 |
| Convulsion | 2 | 2 | 1 |
| Dehydration | 1 | 1 | 1 |
| Dysphagia | 2 | 1 | 1 |
| Febrile convulsion | 2 | 1 | 3 |
| Muscle spasticity | 2 | 2 | 0 |
| Nasopharyngitis | 2 | 1 | 0 |
| Pyrexia | 2 | 0 | 1 |
| Status epilepticus | 0 | 1 | 2 |
| Viral infection | 1 | 1 | 1 |
| Any IDDD-related SAE[b] | 4 | 1 | 1 |
| Device dislocation | 0 | 1 | 0 |
| Device failure | 2 | 1 | 1 |
| Device malfunction | 2 | 0 | 0 |
| Implant site effusion | 1 | 0 | 1 |
| Implant site infection | 0 | 0 | 1 |
| Any treatment-related AE[c] | 4 | 5 | 4 |
| Blood and lymphatic system disorders | 0 | 2 | 0 |
| Eosinophilia | 0 | 2 | 0 |
| Leukocytosis | 0 | 1 | 0 |
| General disorders and administration site conditions | 4 | 2 | 0 |
| Pyrexia | 4 | 2 | 0 |
| Discomfort | 0 | 1 | 0 |
| Investigations (clinical laboratory results) | 4 | 1 | 1 |
| γ-glutamyltransferase increased | 2 | 0 | 1 |
| Alanine aminotransferase increased | 1 | 0 | 0 |
| Blood pressure increased | 1 | 0 | 0 |
| Body temperature increased | 1 | 0 | 0 |
| Eosinophil count increased | 0 | 1 | 0 |
| Skin and subcutaneous tissue disorders | 2 | 2 | 0 |
| Rash | 2 | 1 | 0 |
| Hirsutism | 0 | 1 | 0 |

Figure 9A:
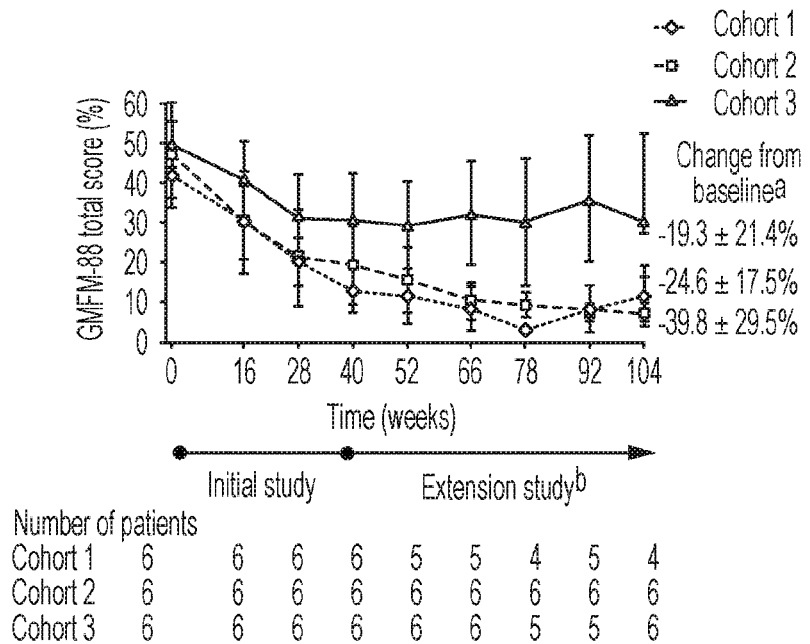
FIGS. 9A and 9B demonstrate the effect of intrathecally delivered rhASA on motor function over 104 weeks of treatment.
Figure 9B:
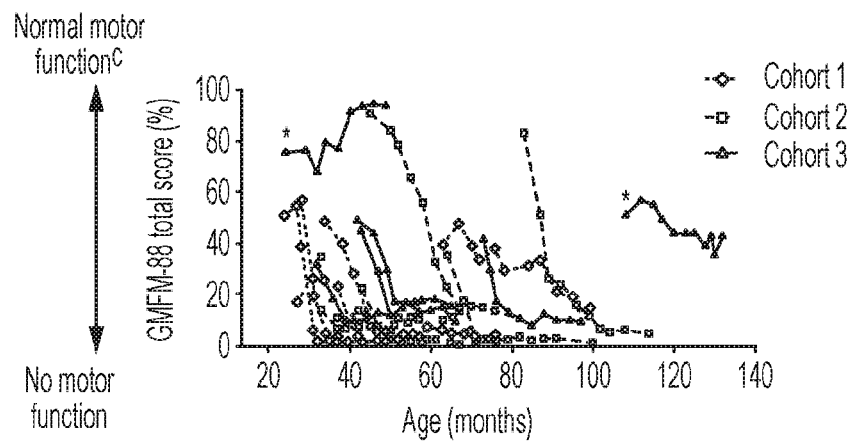

Data are shown as number of patients.
[a]SAEs by preferred terms are given when occurring in at least three patients in the study. All SAEs were judged unrelated to treatment;
[b]Cohort 1 and five patients in cohort 2 received the PORT-A-CATH II at the start of the study. All patients in cohort 3 and one patient in cohort 2 received the SOPH-A-PORT Mini S;
[c]AEs by system organ class are shown when occurring in at least two patients in any group. Preferred terms are shown for each system organ class.
AE, adverse event;
IDDD, intrathecal drug-delivery device;
SAE, serious adverse event Motor Function Mean GMFM-88 total score decreased in all cohorts from baseline to week 104 are shown in FIG. 9A. Two children in cohort 3 (aged 23 and 107 months at treatment initiation) showed evidence of stabilization of their motor function, with absolute GMFM-88 total scores above 40% up to week 104 shown as asterisks in FIG. 9B. At week 104, one of these children (aged 23 months at treatment initiation), had a GMFM-88 total score of 94.3%. This patient's older sibling (also from cohort 3), who started treatment at age 42 months, had a GMFM-88 total score of 12.2% when approximately the same age, and a score of 13.7% at week 104. Mean GMFM-88 total score in healthy children older than 30 months was estimated to be >90% based on the scores for 34 healthy children aged 0-6 years (See, e.g., Sessa M et al. Lancet 2016; 388:476-87). Mean change±standard deviation in GMFM-88 total score from baseline to week 104. After week 40, patients in cohorts 1 and 2 had their doses individually increased (cohort 1, stepwise), with all patients ultimately receiving rhASA 100 mg.

Measures of MLD Severity

Figure 10:
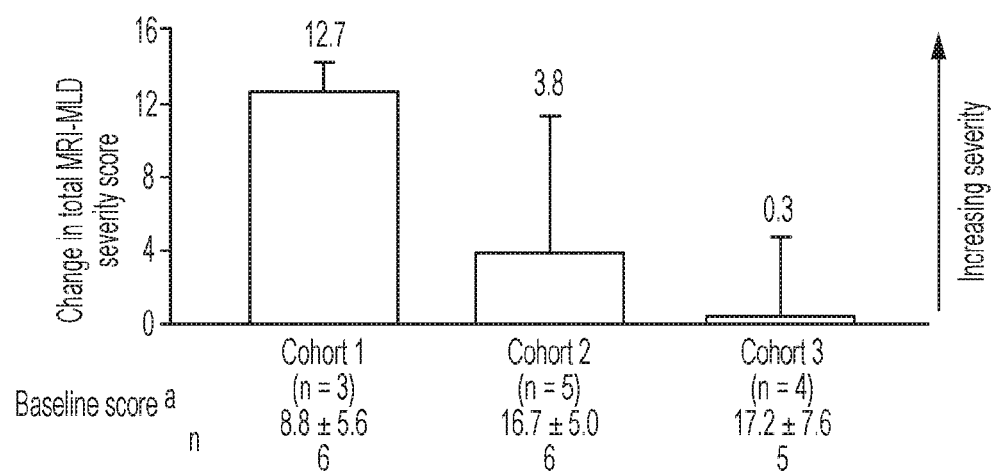
FIG. 10 shows the effect of intrathecally delivered rhASA on MRI-MLD severity score after 104 weeks of treatment. Baseline score is shown as mean±standard deviation total MRI-MLD severity score at baseline (score ranges from 0 to 34, with a higher score indicating greater disease severity).
Figure 11A:
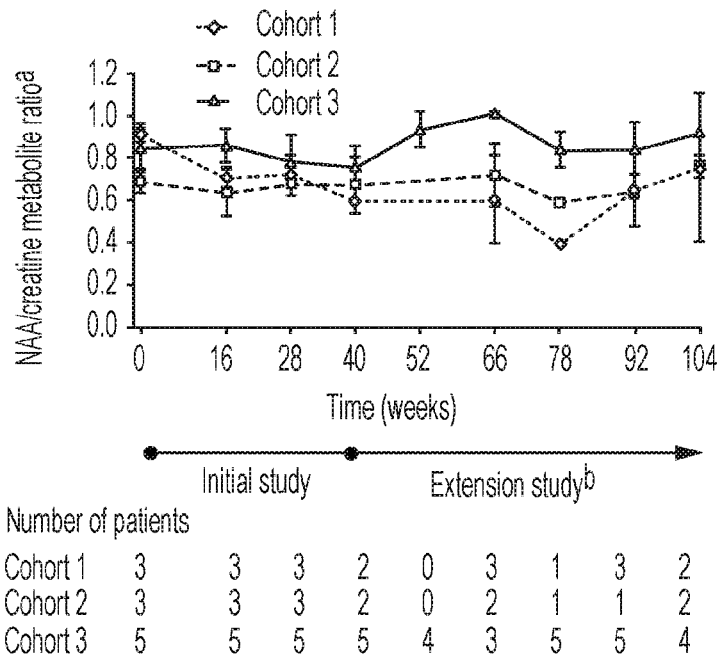
FIGS. 11A and 11B show the effect of intrathecally delivered rhASA on mean NAA/creatine metabolite ratio in brain white matter over 104 weeks of treatment. Right frontal white matter is shown in FIG. 11A and Right frontal-parietal white matter is shown in FIG. 11B. Data are shown as mean±standard error.
Figure 11B:
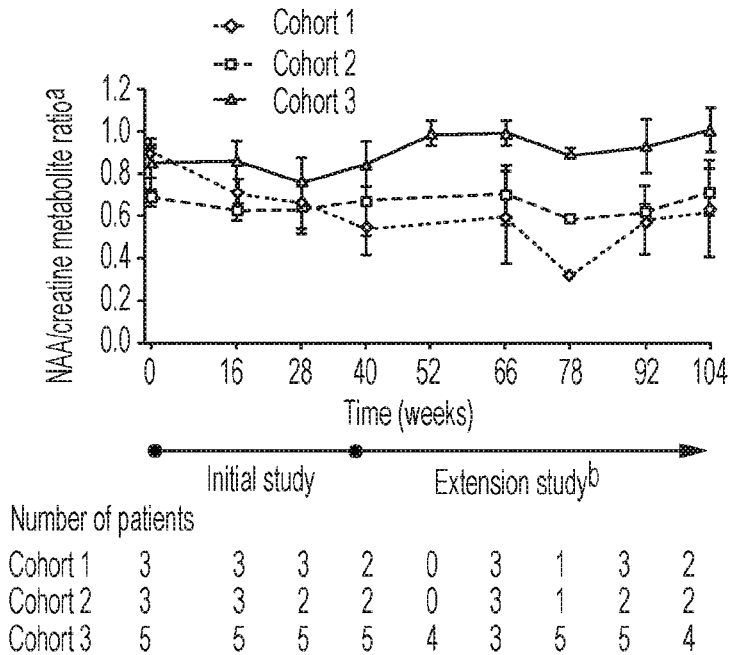

Mean total MRI-MLD severity score increased in cohorts 1 and 2 from baseline to week 104; however, it appeared to be stable over the same period in cohort 3 (FIG. 10). Mean±standard deviation total MRI-MLD severity score at baseline (score ranges from 0 to 34, with a higher score indicating greater disease severity) The effect of intrathecally delivered rhASA on mean NAA/creatine metabolite ratio in brain white matter over 104 weeks of treatment was assessed. Mean NAA/creatine metabolite ratio in frontal (FIG. 11A) and frontal-parietal (FIG. 11B) white matter appeared stable over 104 weeks in cohorts 2 and 3, but tended to decrease in cohort 1. A decrease in the NAA/creatine ratio is indicative of neuronal loss and MLD disease progression. Peri-ventricular white matter NAA/creatine ratio was 1.51-2.30 in four healthy children aged 2.5-6 years (See, e.g., Assadi M et al. J Cent Nerv Syst Dis 2013; 5:25-30).

CSF Sulfatide Concentration

Figure 12:
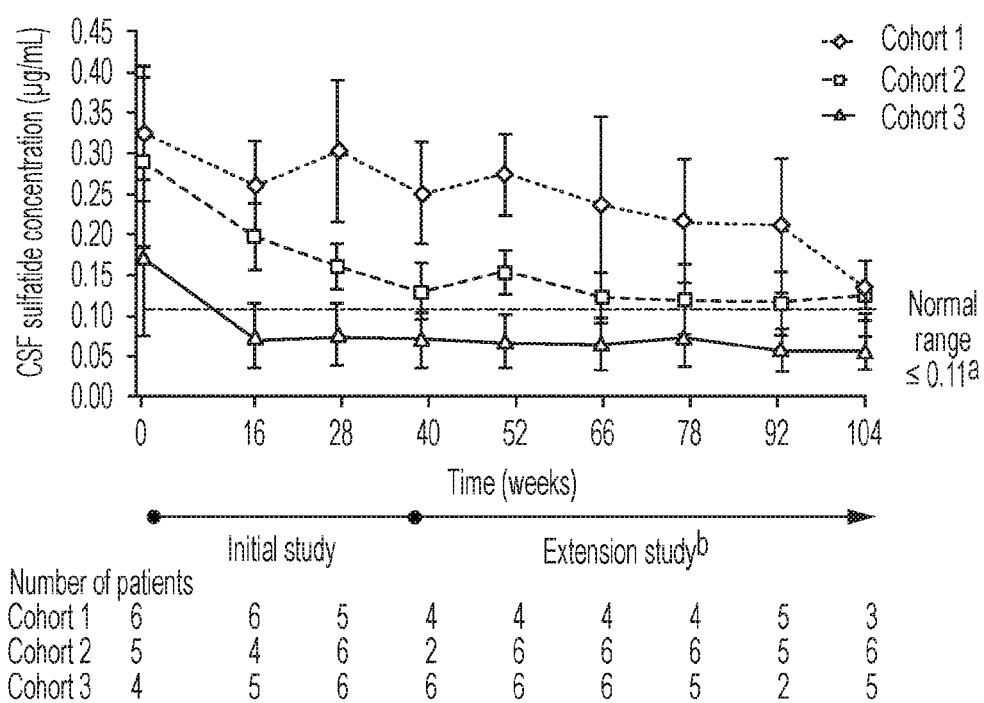
FIG. 12 shows the effect of intrathecally delivered rhASA on CSF sulfatide concentration over 104 weeks of treatment. Data are shown as mean±standard deviation.

Mean CSF sulfatide concentration decreased in all cohorts from baseline to week 104, with cohort 3 being in the normal range (≤0.11 μg/mL, based on CSF samples from 60 pediatric patients) from week 15 (FIG. 12). Baseline CSF sulfatide levels were lower in cohort 3 than in the other two cohorts.

Extension Study Summary

Intrathecally delivered rhASA was well tolerated in children with MLD. Although there was a general decline in motor function over 104 weeks of treatment, there was evidence of a treatment response in patients receiving rhASA 100 mg from the start of the study (cohort 3). There was minimal change in mean MRI-MLD severity score and white matter NAA levels for cohort 3. Two patients in cohort 3 showed stabilization of motor function. A treatment response was not apparent in cohorts 1 and 2. One child in the study may be atypical for late-infantile MLD and more representative of juvenile MLD. These findings support the continued development of intrathecally delivered rhASA as a potential treatment for patients with late infantile MLD. An additional six children (cohort 4) were subsequently enrolled in the study and are currently receiving rhASA 100 mg every other week.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

We claim:

1. A method of treating metachromatic leukodystrophy (MLD) comprising
determining brain lesion involvement using magnetic resonance imaging (MRI) to obtain an MLD MRI severity score,
administering intrathecally to a subject in need of treatment a recombinant arylsulfatase A (ASA) enzyme at a therapeutically effective dose of greater than 100 mg and an administration interval for a treatment period of at least 6 months sufficient to stabilize or reduce brain lesion involvement relative to baseline; and
assessing brain lesion involvement by the MLD MRI severity score.

2. The method of claim 1, wherein administering the recombinant ASA enzyme results in stabilization of the MLD MRI severity score in the subject relative to baseline.

3. The method of claim 1, wherein the subject is human.

4. The method of claim 1, wherein the treatment interval is at least weekly.

5. The method of claim 1, wherein the administration interval is every other week.

6. The method of claim 1, wherein the therapeutically effective dose is less than 200 mg.

7. The method of claim 1, further comprising determining levels of a biomarker that is decreased in MLD in a brain tissue relative to a baseline level of the biomarker.

8. The method of claim 7, wherein the biomarker is N-acetylaspartate (NAA).

9. The method of claim 8, wherein levels of N-acetylaspartate (NAA) are assessed by proton magnetic resonance spectroscopy.

10. The method of claim 9, further comprising measuring NAA/creatine metabolite ratio.

11. The method of claim 1, wherein administering the recombinant ASA enzyme results in decreased levels of a biomarker that accumulates in MLD in a bodily fluid selected from the group consisting of cerebrospinal fluid, urine, blood, and blood serum relative to a baseline level of the biomarker.

12. The method of claim 11, wherein the biomarker is selected from the group consisting of sulfatide, lysosulfatide, and combinations thereof.

13. The method of claim 12, wherein administering the recombinant ASA enzyme results in a decrease of sulfatide levels in the cerebrospinal fluid (CSF) relative to baseline.

14. The method of claim 1, wherein administering the recombinant ASA enzyme further results in improvement, stabilization or reduction decline of one or more cognitive, adaptive, and/or executive functions.

15. The method of claim 1, wherein the subject is 16 years old or younger.

16. The method of claim 1, wherein the subject is three years old or younger.

\* \* \* \* \*